(12) United States Patent
Ohtomo et al.

(10) Patent No.: US 6,908,750 B2
(45) Date of Patent: Jun. 21, 2005

(54) GENE ENCODING HM1.24 ANTIGEN PROTEIN AND PROMOTER THEREOF

(75) Inventors: Toshihiko Ohtomo, Gotenba (JP); Masayuki Tsuchiya, Gotenba (JP); Yasuo Koishihara, Gotenba (JP); Masaaki Kosaka, Tokushima (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/423,007

(22) Filed: Apr. 25, 2003

(65) Prior Publication Data

US 2003/0180889 A1 Sep. 25, 2003

Related U.S. Application Data

(62) Division of application No. 09/622,166, filed as application No. PCT/JP99/00884 on Feb. 25, 1999, now Pat. No. 6,613,546.

(30) Foreign Application Priority Data

Feb. 25, 1998 (JP) .............................................. 10-60617
Mar. 24, 1998 (JP) .............................................. 10-93883

(51) Int. Cl.$^7$ ........................ C12N 15/00; C12N 15/85; C12N 15/63; C07H 21/04
(52) U.S. Cl. ................... 435/69.1; 435/325; 435/320.1; 536/24.1; 536/23.5
(58) Field of Search ............................. 435/69.1, 325, 435/320.1; 536/24.1, 23.5; 800/8

(56) References Cited

FOREIGN PATENT DOCUMENTS

JP          7-196694         8/1995

OTHER PUBLICATIONS

Ohtomo, et al, 1999, Biochem. Biophys. Res. Comm. 258: 583–591.*
Smith et al., 1997, Nature Biotechnology 15: 1222–1223.*
Brenner, S., 1999, Trends in Genetics 15: 132–133.*
Spek, et al., 1995, J. Biol. Chem. 270(41): 24216–24221, esp. p 24218.*
Wang, A., et al, 1999, Nuc. Acids Res. 27(23): pp 4609–4618, esp. p 4615.*
Kaufman, et al, 1999, Blood, 94(9): 3178–3184.*
Hillier et al., "Soares Fetal Liver Spleen 1 NFLS S1 Home Sapiens cDNA Clone Image:462339 3', mRNA Sequence," Database EMBL Online, Jan. 5, 1998, 1 Sheet, XP-002229573.
Ohtama et al., "Molecular Cloning and Characterization of a Surface Antigen Preferentially Overexpressed on Multiple Myeloma Cells," Biochemical and Biophysical Research Communications, Academic Press Inc., vol. 258, No. 3, May 19, 1999, pp. 583–591, XP-002950705.
T. Goto et al., "Analysis of Myeloma cell surface antigens using new monoclonal antibodies recognizing plasma Cell-related antigens", Japan. J Clinic. Immun., 15(6); pp. 688–691, 1992.
Ishikawa, et al, "Molecular cloning and chromosomal mapping of a bone marrow stromal cell surface gene, BST2, that may be involved in pre-B-cell growth", Genomics 26, pp. 527–534, 1995.
T. Goto et al., A novel membrane antigen selectively expressed on terminally differentiated human B cells Blood, vol. 84, No. 6, pp. 1922–1930, 1994.
Supplementary European Search Report, issued in European Application No. EP 99 90 6488, dated Feb. 24, 2003.
Database EMBL, Jan. 5, 1998, Hillier, L., et al. XP 002229573.
Spek et al. (1995), J. Biol. Chem., vol. 270, No. 41, pp. 24216–24221.
Brenner, (1999), Errors in Genome Annotation, Trends in Genetics, vol. 15, No. 4, pp. 3–4.
Smith et al., (1997), The Challenges of Genome Sequence Annotation or "The Devil is in the Details", Nature Biotechnology, vol. 15, pp. 1222–1223.
Kaufman et al., (1999), Blood, vol. 94, No. 9, pp. 3178–3184.
Wang et al., (1999), Nuc. Acids, Res., vol. 27, No. 23, pp. 4609–4618.

* cited by examiner

Primary Examiner—Elizabeth Kemmerer
Assistant Examiner—Sandra Wegert
(74) Attorney, Agent, or Firm—Foley & Lardner LLP

(57) ABSTRACT

There are provided a genomic DNA comprising 4 exons encoding the amino acid sequence as set forth in SEQ ID NO: 2 and 3 introns ligating them, and a splicing variant of said genomic DNA; as well as a DNA having the base sequence as set forth in SEQ ID NO: 4 and a promoter activity and the fragment thereof, and uses thereof.

11 Claims, 18 Drawing Sheets

Fig. 1

```
GAATTCGGCACGAGGATCTGGATGGCATCTACTTCGTATGACTATTGCAGAGTGCCCAT     60
                M   A   S   T   S   Y   D   Y   C   R   V   P   M      13
GGAAGACGGGGATAAGCGCTGTAAGCTTCTGCTGGGGATAGGAATTCTGGTGCTCCTGAT    120
 E   D   G   D   K   R   C   K   L   L   L   G   I   I   L   V   L   L   I    33
CATCGTGATTCTCGGGGTGCCCCTTGATTATCTTCACCATCAAGGCCAACAGCGAGGCTG    180
 I   V   I   L   G   V   P   L   I   I   F   F   T   I   K   A   N   S   E   A   C    53
CCGGGGACGGGCTTCGGGCAGTGATGGAGTGTCGCAATGTCACCCATCTCCTGCAACAAGA    240
 R   D   G   L   R   A   V   M   E   C   R   N   V   T   H   L   L   Q   Q   E    73
GCTGACCGAGGCCCAGAAGGGCTTTCAGGATGTGGAGGCCCAGGCTGCCACTTGCAACCA    300
 L   T   E   A   Q   K   G   F   Q   D   V   E   A   Q   A   A   T   C   N   H    93
CACTGTGATGGCCCTAATGGCCCTTCCCCTGGATGCAGAAAAGGCCAAGGACTTCAGGACGTCTGCAGA    360
 T   V   M   A   L   M   A   S   L   D   A   E   K   A   Q   G   Q   K   K   V    113
GGAGGAGCTTGAGGGAGAGATCACTACATTAAACCATAAGCTTCAGGACGCGTCTGCAGA    420
 E   E   L   E   G   E   I   T   T   L   N   H   K   L   Q   D   A   S   A   E    133
GGTGGAGCGACTGAGAGAAGAGAAACCAGGTCTTAAGCGTGAGAATCGGACAAGAAGTA    480
 V   E   R   L   R   R   E   N   Q   V   L   S   V   R   I   A   D   K   K   Y    153
CTACCCCAGCTCCCAGGACTCCAGCTCCGGCGGCCCCGCTCCGCCGCTGCTGATTGTGCT    540
 Y   P   S   S   Q   D   S   S   A   A   A   P   Q   L   L   I   V   L   L       173

(SEQ ID NOS: 1 AND 3)
```

Fig.2

```
GGGCCTCAGCGGCTCTGCTGCAGTGAGATCCCAGGAAGCTGGCACATCTTGGAAGTCCGT    600
 G  L  S  A  L  L  Q  *                                          180
CCTGCTCGGCTTTTCGCTTGAACATTCCCTTGATCTCATCAGTTCTGAGCGGGTCATGGG    660
GCAACACGGTTAGCGGGAGAGCACGGGTAGCCGGAGAAGGGCCTCTGGAGCAGGTCTG      720
GAGGGGCCATGGGGCAGTCCTGGGACACAGTCGGGTTGACCCAGGGCTGTCTC           780
CCTCCAGAGCCTCCCCGACAATGAGTCCCCCCTCTTGTCTCCCACCCTGAGATTGGG       840
CATGGGTGCGGTGTGGGGCATGTGCCTGCTGTGTTATGGTTTTTTTTGCGGGGGG         900
GGTTGCTTTTTCTGGGTCTTTGAGCTCCAAAAATAAACACTTCCTTTGAGGGAGAG        960
CACACCCTTAAAAAAAAAAAAAAAAAAAAAATTCGGGGGCCGCCA                   1014

(SEQ ID NOS: 1 AND 3)
```

LANE 1: KPMM2 (5 × 10⁵ CELLS EQUIVALENT)
LANE 2: RPMI8226 (25 × 10⁵ CELLS)
LANE 3: U266 (25 × 10⁵ CELLS)
LANE 4: CHO/HM (5 × 10⁵ CELLS)
LANE 5: CHO/NEO (5 × 10⁵ CELLS)
LANE 6: NONE
LANE 7: KPMM2 (5 × 10⁵ CELLS)
LANE 8: CHO/HM (5 × 10⁵ CELLS)

Fig.7

```
ACTAAAAGTCTCTGATATGCAGAAATAATGGCATAAGCTGTCTTTCTGTCTGTCCCCTCTCTCTCT  -1919
                NF-IL6
GCCTCGGCTGCCAGGCAGGAAGGCCCCCCTGTCCAGTGGACACGTGACCCACATGACCTTACCTATCAT  -1849
                                                              GATA1
TGGAGAATGACTCACACTCTTTACCCTGCCCCCTTTGCTTTGTATCCAATAAATAACAGCACAGCCAGACA  -1779
          AP-1
TTCGGGGCCACTACCAGTCTCCGGCGCATTGCTGCTGGTAGTGGTCCCCGGCCCAGCTGTCTTTCTTTTAT  -1709
                                                                  GATA1
                                  AP-2
CTCTTCGTCTGTGTCTTTATTTCTACACTCTCTCGTCGCCGCACACAGGGAGAGACCCACTGACCCTGT  -1639
Sp1
GGGGCTGGTCCCTACAGTAATTTAAAGGGAAGAGCAACAAACTTTCGGTTTGCAGGGCTGGGACTGTTT  -1569
ACAGCTGCAAAATTTAGAGAGGACATCAATCTATTATTCCACATTTTACAGCTGGGGAAATCAATGCT  -1499
                                                        NF-IL6
AAGAGAGGAAATTCATTTGCCCAGAGGTGCACCACCTGGCCTCCAATGTGCAATTCATGCAATTGTGAT  -1429
        AP-1
TTCCGACCTGGTCCCAAACTAACCCTAAAGTTAGCAGGCCAGAGAACAGTGCTGCTCAAATAAGTCAGCTTA  -1359
GTCAAATAAGTCAGGCAAAGGTCGTGTCTTTGCCACCTGGAGTCCTGGCCAGGCTGGTAGGTCCCTCCTCC  -1289
TGGGACAAGTTCACCCTCCAGAATTTCAGCAAGATCATCTCCCACAGCTTGTTAATTGGTTCTTGGTTCT  -1219
                                NF-IL6
AAGTGATTTTTTGTTTATTGGTTTAAGAGATGGGATCCCCACTCTATCACCCAGGCTTGAGTGCCGTGGC  -1149
ACAATCATAGCTCGCTGCAGCCTCAAACTCCTGAGTCGATCCTCCTGCCCTCCAGCCTCCCAGCCCTC  -1079
GATA1
AGCCTGGGACCAGGCATGTACCACCATGCCTGGCTCTAAGTGGCTTTAAATGGGGTCCTTCTGAGGGAT  -1009
GTTGGAGTCAGGGCCTCAGGGCCCTGGGGGAGTTCCCAGGCCTTCTCGGGAGGCTCTGGACTTGACCTCGCC  -939
                        NF-kB   AP-2                  AP-2
```

(SEQ ID NO: 4)

Fig.8

```
TACTGTCTGGCCCTGCTGAAAGAAAAAAAACATGGAAATGGCAGACCTAACAGAATCTGGCCTGTGGT    -869
CAGGATGTGGCTGAAGAAGCCACAAGAAAAAAACATGCCAGTCCCCTTTCAGCGGTCATGCCAGCAGTTGGG    -799
TGCCGATAATGGGCCTGATTTCCTAGGAAGCCCTGGCTCTCTTGGCCACAGTGTCTGAGGCT    -729
                        NF-IL6                                 AP-2
GGCCCTGTTATTCCCCTTTGCAGATGAAGAAACAGGCTCAGAGAGTTTACCTGGTATCCTGGAGTCCCAG    -659
GAGCACTTTTCTGGAAGTAGGAGCTTGTTCCTGCAGTGCCAAGACAGAGACCGACATTGTTTGTTGG    -589
     NF-IL6
CTGGGTCGGTCCCAGTTTCAGCTGCTCCACCTGTTGCTCACACCCTGCTCACATGTCTCCCA    -519
TAGTCCCCTGGGTGGGGACAGAGGCCACTGGATGAAGCCCTGCTGTCGTCACCAGAGACACCTGAACACAA    -449
    AP-2                                                CREB
AAACCAGTCCCTGGGGTCAGACCCCTGCCCTGCCCTCACTCCACCACGCAA    -379
                        Sp1/AP-2            AP-2
CTGTGCAACCTCAGTTTCCCCAGGTGGAGACCGGACCAACAATGATGGCCTCTGCCTCTTCAGGTCATAG    -309
TACAGATGAATACAGGCTGGCACGGCTGGACACTCAGTAACACACGGCAGAGGCACAGGGACTTAAGAT    -239
GGAGTGTCCCAGGCAGCAGCCACCAGCCACCCAGTTGGCTGCACCCAGTGGGAAGGGCCAAGGGCTTTTAAAGCAGGGT    -169
                                            AP-2
GAAAAAAAAAGCCCCACCTCCTTTCTGGGAAACTGAAACCTAATTAATCCTCTGCCTGTAGGTG    -99
                STAT3    STAT3
CCTCATGCAAGAGCTGTGGTCAGAGCACTTCCTGGAACTTGCTATTGGTCAGGACGTTTCCTATGCTAA    -29
                ISGF3                STAT3                           TRF
TAAAGGGGTGGCCCGTAGAAGATTCCAGCACCCCTAACTCCAGGCCAGACTCCTTTCAGCTAAAGG    +41
 AP-2
GGAGATCTGGATGGCATCTACTTCGTATGAC    +72
 M A S T S Y D
```

(SEQ ID NOS: 4 AND 21)

(A)

(B)

| | | |
|---|---|---|
| AP2 (19 mer) | ; 5'- ACTATAGGGC ACGCGTGGT -3' | (SEQ ID NO: 9) |
| P1 (25 mer) | ; 5'- CCTCGCTGTT GGCCTTGATG GTGAA -3' | (SEQ ID NO: 10) |
| HM3 (18 mer) | ; 5'- GCCAACAGCG AGGCCTGC -3' | (SEQ ID NO: 11) |
| S4 (18 mer) | ; 5'- GCATCCAGGG AAGCCATT -3' | (SEQ ID NO: 12) |
| INT3 (18 mer) | ; 5'- ACTCCCCAGG CCAAAACC -3' | (SEQ ID NO: 13) |
| HM4a (22 mer) | ; 5'- CGCGTCCTGA AGCTTATGGT TT -3' | (SEQ ID NO: 14) |
| HM5 (18 mer) | ; 5'- GCGTCTGCAG CGGTGGAG -3' | (SEQ ID NO: 15) |
| HM3a (18 mer) | ; 5'- CGAAAAGCCG AGCAGGAC -3' | (SEQ ID NO: 16) |

Fig.11

```
                                                                                              70
CCCTCCCCTAACTCCAGGCCAGAGACTCCTTTCAGCTAAAGGGGAGATCTGGATGGCATCTACTTCGTATGA
                                      M  A  S  T  S  Y  D                                   140
CTATTGCAGAGTGCCCATGGAAGACGGGGATAAGCGCTGTAAGCTTCTGCTGGGGATAGGAATTCTGGTG
 Y  C  R  V  P  M  E  D  G  D  K  R  C  K  L  L  L  G  I  G  I  L  V                       210
CTCCTGATCATCGTGATTCTGGGGGTGCCCCTTGATTATCTTCACCATCAAGGCCAACAGCGAGGCCTGCC
 L  L  I  I  V  I  L  G  V  P  L  I  I  F  T  I  K  A  N  S  E  A  C  R                    280
GGGACGGGCCTTCGGGCAGTGATGGAGTGTCGCAATGTCACCCATCTCCTGCAACAAGAGCTGACCGAGGC
 D  G  L  R  A  V  M  E  C  R  N  V  T  H  L  L  Q  Q  E  L  T  E  A                       350
CCAGAAGGGCTTTCAGGATGTGGAGGCCCAGGCCCGCACCTGCAACCACACTGTGgtaagctcctcaact
 Q  K  G  F  Q  D  V  E  A  Q  A  A  T  C  N  H  T  V                                      420
cctttggatggcctagtactaggcggtgggaggacaagaatctctcccccagaaatctgaccaggqtgg
                                                                                            490
gtctccaggagatgcagggaggtcctgaaactgctcctgggcccccacatcaagggacctaggttccc
                                                                                            560
ctaccaqqqtttgtgggccccctaaccagtccaggcactggtgtagggcaggtgttaaaactctcca
                                                                                            630
gatccccccaaatcggggaccttcagtatccctgggactaggtgaatttataaattcttttccaggcac
                                                                                            700
tggtgtcggggcccttgaaactgccttggcaccagtcctgggagtagaatcccctattcaggqttg                774
aaggggaccctcaccagatatggggatcttgaaactcttcactt[c]actgtcacttgggcggggaaatccact     844
cacctggtcctgatattggtagggccctcctaactttctcttgggcatgtctgctgctcaggcaatctgaaatgtccact        914
gcattctgatttgttatcgatagcctccaagtttccacgtgggtggcctcaaaactcccatttgaggaccca                984
aaactttggttatcgatagcctccaagtgttgtgtgcatttgcatttaagttgagaccatggtgcag                    1054
catgcttatgggtggccctgggagagtgtgtggctgttcttttaaggttgggagaccactagggaggagg              1124
agaggggttggaagaaaaacctgaaagggtttgcatttaagccccctctgtcccaggacctagggaggagg              1194
cccaggtcccaggggcagcagccaaaactcccaggccaaaaccccagattctaactcttctttagATGGCC
                                                                           M  A
```

(SEQ ID NOs: 2 AND 3)

Fig.12

```
CTAATGGCTTCCCTGATGCAGAGAAGGCCAAGAGACAAAAGAAAAGTGGAGGAGCTTGAGGgtgagaaag        1264
 L  M  A  S  L  D  A  E  K  A  Q  G  G  Q  K  K  V  E  E  L  E  G
ggagaaggagagaggggccggggaggggtgagtcaggtatggaagagaggggtggggcaggagaccagggc        1334
tggaggttgggtaaggggaggttctgtcccagagtggagcaggcgccccagcatgcccacatgctgacc        1404
cgcccccctgttctgtcctcccaccctaccagGAGAGATCACTACATTAAACCATTAAGCTTCAGGACGCG       1474
                                  E  I  T  T  L  N  H  K  L  Q  D  A
TCTGCAGAGGTGGAGCGACTGAGGtcagagagatagccttcccccgctaccctccacctgccacattcctct      1544
 S  A  E  V  E  R  L  R
caccccacatccctagcccaagaccccaggatctcctttgctcccaaatcccattgcccaaggata            1614
aagtttgagtcccacaaaaggataacttagcccctaggtcacagagccatggggtggcgctgtccattc         1684
cctccccggtgacttggattgggcggtgcggggaactcccggggcggtgggcttacaggagggcg             1754
gcaggagccaggagcagagcagatgcctgattgccccccatctgtaccgcagAAGAGAAAACCAGGTCTTAA      1824
                                                       R  E  N  Q  V  L  S
GCGTGAGAATCGGGACAAGAAGTACTACCCCAGCTCCCAGGACTCCCCAGCTCCGGCGCCCCCAGCT           1894
 V  R  I  A  D  K  K  Y  Y  P  S  S  Q  D  S  S  S  A  A  A  P  Q  L
GCTGATTGTGCTGCTGGGCCTCAGCGCCTCTGCTGCAGTGAGATCCCAGGAAGCTGGCACATCTTGGAAGG      1964
 L  I  V  L  L  G  L  S  A  L  L  Q
TCCGTCCTGCTCGGCTTTCGCTTGAACATTCCCTTGATCTCATCAGTTCTGAGCGGGTCATGGGCAAC          2034
ACGGTTAGCGGGAGAGCACGGGGTAGCCGGAGAAGGCCCTCTGGAGCAGGTCTGGAGGGCCATGGGGGC         2104
AGTCCTGGGGTGTGGGACACAGTCGGGTTGACCCCAGGCTGTCTCCCCAGAGCCTCCCTCCGACAAT           2174
GAGTCCCCCCTCTGTCTCCCACCCTGAGATTGGGCATGGCGGTGCGGTGTGGGGGCATGCTGCCTGT           2244
TGTTATGGGTTTTTTGCGGGGGGTTGCTTTTTTCTCGGGGTCTTTGAGCTTCCAAAAA AATAAACACT         2314
TCCTTTGAGGGAGAGCACACCTT 2337
```

(SEQ ID NOS: 2 AND 3)

Fig.13

```
ATGGCATCTACTTCGTATGACTATTGCAGAGTGCCCATGGAAGACGGGGATAAGCGCTGT    60
MetAlaSerThrSerTyrAsnTyrCysArgValProMetGluAspGlyAspLysArgCys

AAGCTTCTGCTGGGCATAGGAATTCTGGTGCTCCTGATCATCGTGATTCTGGGGGTGCCC   120
LysLeuLeuLeuGlyIleGlyIleLeuValLeuLeuIleIleValIleLeuGlyValPro

TTGATTATCTTCACCATCAAGGCCAACAGCGAGGCCTGCCGGGACGGCCTTCGGGCAGTG   180
LeuIleIlePheThrIleLysAlaAsnSerGluAlaCysArgAspGlyLeuArgAlaVal

ATGGAGTGTCGCAATGTCACCCATCTCCTGCAACAAGAGCTGACCGAGGCCCAGAAGGGC   240
MetGluCysArgAsnValThrHisLeuLeuGlnGlnGluLeuThrGluAlaGlnLysGly

TTTCAGGATGTGGAGGCCCAGGCCGCCACGTGCAACCACACTGTGAAGAGAAAACCAGGT   300
PheGlnAspValGluAlaGlnAlaAlaThrCysAsnHisThrValLysArgLysProGly

CTTAAGCGTGAGAATCGCGGACAAGAAGTACTACCCCAGCTCCCAGGACTCCAGCTCCGC   360
LeuLysArgGluAsnArgGlyGlnGluValLeuProGlnLeuProGlyLeuGlnLeuArg

TGCGGCGCCCCAGCTGCTGATTGTGCTGCTGGGCCTCAGCGCTCTGCTGCAGTGAGATCC   420
CysGlyAlaProAlaAlaAspCysAlaAlaGlyProGlnArgSerAlaAlaValArgSer

CAGGAAGCTGGCACATCTTGGAAGGTCCGTCCTGCTCGGCTTTTCGCTTGA           471
GlnGluAlaGlyThrSerTrpLysValArgProAlaArgLeuPheAla*
```

(SEQ ID NOs: 19 AND 20)

——— : PART DIFFERENT IN AMINO ACID SEQUENCE
FROM HM1.24 ANTIGEN PROTEIN

Fig. 14

```
6 s
          10         20         30         40         50         60
     tcccatagtcccctcggtggggacagaggcactggatgaagccctgctcgtcaccacaga
         70         80         90        100        110        120
     gacacctgaacacaaaaaccagtccctgggtcagacccccaggccccccagacccag
        130        140        150        160        170        180
     gccctgccctcactccaccacgcaactgtgcaacctcagtttcccaggtggagaccgga
        190        200        210        220        230        240
     ccaacaatgatggcctctgcctcttcaggtcatagtacagatgaatacaggctggcacgg
            a
        250        260        270        280        290        300
     cctaggcactcagtaacacacggcagaggcacagggacttaagatggagtgtcccaggca
                                    a
        310        320        330        340        350        360
     gccacagttggctggcaccccagttgggaagggcccaagggcttttaaagcagggtgaaaa
                                c
        370        380        390        400        410        420
     aaaagcccacctcctttctggggaaactgaaaacctaattaatcctctgcctgt
         del
        430        440        450        460        470        480
     aggtgcctcatgcaagagctgctggtcagagcacttcctgaacttgctattggtcagga
8s      490        500        510        520        530        540
     cgtttcctatgctaataaaggggtgcccgtagaagattccagcacccctcccctaactcc
```

SEQ ID NO: 33

Fig. 15

```
         550          560           570          580         590          600
    aggccagactcctttcagctaagggggagatctggATGGCATCTACTTCGTATGACTATC
                     deletion          M  A  S  T  S  Y  D  Y  C
                                                    BST2B
         610          620          630         640          650         660
    GCAGAGTGCCCATGGAAGACGGGGATAAGCGCTGTAAGCTTCTGCTGGGGATAGGAATTC
     R  V  P  M  E  D  G  D  K  R  C  K  L  L  L  G  I  G  I  L
                                         BST2-R3
         670         680          690         700          710         720
    TGGTGCTCCTGATCATCGTGATTCTGGGGGTGCCCTTGATTATCTTCACCATCAAGGCCA
     V  L  L  I  I  V  I  L  G  V  P  L  I  I  F  T  I  K  A  N
         730         740          750         760          770         780
    ACAGCGAGGCCTGCCGGGACGGGCCTTCGGGCAGTGATGGAGTGTGCATGTCACCCATCC
     S  E  A  C  R  D  G  P  S  G  S  D  G  V  C  M  S  P  H  L
         790         800          810         820          830         840
    TCCTGCAAGAGAGCTGACCGAGGCCCAGAGGCTTTCAGGATGTGGAGGCCCAGGCCG
     L  Q  E  A  D  R  G  P  E  A  F  Q  D  V  E  A  Q  A  A
         850          860         870         880          890         900
    CCACCTGCAACCACCACTGTgtaagctcctcaactcctttggatgcctagtactaggcg
      T  C  N  H  H  C
         910         920          930          940         950         960
    gtgggaggacaagaatctctctcccagaaatctgacccagggtgggtctccagggagatg
         970         980          990         1000         1010         1020
    caggggaggtcctgaaactgctcctggccccacatcaagggacctaggttcccctacc
```

(SEQ ID NOS: 3 AND 33)

Fig.16

```
     1030      1040      1050      1060      1070      1080
agggtttgtgggcccctaacccagtccaggcactggtgtagggcagggtgttaaaact 1090      1100      1110      1120      1130      1140
ctccagatcccccaaatcggggacctcagtatcccctgggacttaggtgaatttataaa 1150      1160      1170      1180      1190      1200
ttctttccagggcactggtgtgtcgggggcctgaaactcctcgtgggcaccagtcctgggg 1210      1220      1230      1240      1250      1260
                       HMINT1F
gagtagaaatccctattcagggttgaaggggggacctcaccagacccctgaaaaaggggct 1270      1280      1290      1300      1310      1320
tttgaaatttcacttcatccctaaggaactgaaatattcacctgggtggtgatatgggg
                                                        1380

1390      1400      1410      1420      1430      1440
gatcttgaaactctcgctgggcatgtcacttgggcggggaaatccactgcattctggat 1390      1400      1410      1420      1430      1440
ttggtagggccctctaacttttcttggccattgctcaggcaatctggaaatgtccacta 1450      1460      1470      1480      1490      1500
aactttggttatcgatagcctccaagttccacgtggggtgcctcaaaactcccattttt 1510      1520      1530      1540      1550      1560
gaggaccacatgcttatgggtggccctgggagagtgtgtggttgtggctgttctttaag 1570      1580      1590      1600      1610      1620
gttggagaccatggtgcagagagggttggaagaaaacctgaaaggggtttgcatttaagc
```

SEQ ID NO: 33

Fig.17

```
                1630      1640      1650      1660      1670      1680
           ccctctgtccccagagaccctagggaggagggcccaggtcccaggggcagcagccaaactccc
                                                         HMEX2F
                1690      1700      1710      1720      1730      1740
           caggccaaaacccagattctaactcttcttagATGGCCCTAATGGCTTCCCTGGATGCA
                                              M  A  L  M  A  S  L  D  A GAGAAGGCCAAGGACAAAGAAAGTGGAGGAGCTTGAGGgtgagaaaggggagaaagggag
            E  K  A  K  D  K  E  S  G  G  A  *
                                        HMEX2R
                1810      1820      1830      1840      1850      1860
           agggccggggagggggtgagtcaggtatggaagagaggggtggggcagggagaccagggct
                1870      1880      1890      1900      1910      1920
           ggaggttgggggtaaggggggaggtttctgtcccagagtggagcagggccccagcatggccac
                1930      1940      1950      1960      1970      1980
           atgctgaccccgccccctgtttctgtcctcccacctaccaggAGAGATCACTACATTAAA
                                                      E  I  T  T  L  N
           HMEX3F      1990      2000      2010      2020      2030      2040
           CCATAAGCTTCAGGACACGGCTCTGCAGAGGTGGAGGACTGAGgtcagagatagccttccc
            H  K  L  Q  D  T  A  L  Q  R  W  R  T  E
                2050      2060      2070      2080      2090      2100
           ccgctaccctccacctgccacattcctctcaccccacatccctagcccaagacccagga
```

(SEQ ID NOs: 3 AND 33)

Fig. 18

```
       2110      2120      2130      2140      2150      2160
tctcctttgctctcccaaaatcccccattgccccaagggataaagtttgagtcccacaaagg
       2170      2180      2190      2200      2210      2220
ataacttagcccctagggtcacagagagccatgggtggccgctgtccattccctcccggtg
       2230      2240      2250      2260      2270      2280
acttggattggggcggtgcggggggaactcccggggcggtgggcttacagggaggggcgg
       2290      2300      2310      2320      2330
caggagccaggacgagcagatgcctgattgcccccatctgtaccgcagAAGAGAAAACCC
                                             Met              R  E  N  Q
       2350          2360            2370        2380         2390       2400
AGGTCTTAAGCGTGAGAATCGCGGACAAGAAGTACTACCCAGCTCCCAGGACTCCAGCT
 S   L   S   V   R    I   A   D   K   K   Y   Y   P   A   P   D   S   S
          2410          2420         2430         2440         2450       2460
CCGCTGCGGGCCCCAGCCTGCTGATTGTGCTGGGGCTTCAGCGCTCTGCTGCAG
 P   L   R   A   P   A   C   C   L   I   V   L   G   L   S   A   L   Q
                                                              BST2-R1

(SEQ ID NOS: 3 AND 33)
```

GENE ENCODING HM1.24 ANTIGEN PROTEIN AND PROMOTER THEREOF

TECHNICAL FIELD

The present invention relates to a genomic gene encoding HM1.24 antigen protein, a promoter of the gene encoding HM1.24 antigen protein, and uses thereof.

BACKGROUND ART

Mouse anti-HM1.24 monoclonal antibody has been prepared using a human myeloma cell line KPC-32 as an immunogen (Goto, T. et al., Blood 84: 1922–1930, 1994). The HM1.24 antigen that is recognized by this antibody is a membrane protein having a molecular weight of 29 to 33 kDa that is overexpressed on the surface of myeloma cells. Furthermore, for normal cells its expression has been confirmed in immunoglobulin-producing B cells (plasma cells, lymphoplasmacitoide cells), but expression is rarely observed in the other cells and tissues (Goto T. et al., supra). However, nothing is known about HM1.24 antigen except its expression distribution and molecular weight.

According to the present invention, as a result of the cloning of genomic DNA encoding HM1.24 antigen, the determination of its nucleotide sequence and the deduced amino acid sequence, and further homology search, HM1.24 antigen was demonstrated to be a molecule identical with BST2 that is a surface antigen expressed on the stroma cells isolated from the bone marrow of patients with myeloma, and the bone marrow and the snynovial membrane of patients with rheumatoid arthritis. BST2 has been shown to have an ability of supporting the growth of pre-B cells and is thought to be involved in the pathology of rheumatoid arthritis, but its other physiological functions are not known (Ishikawa J. et al., Genomics 26: 527–534, 1995).

In the production of a useful gene product derived from an animal by means of genetic engineering, it often happens that the gene is not expressed, a gene product, protein, does not take a correct conformation, post-translational modification does not occur correctly and the like, when a microorganism host such as *Escherichia coli, Bacillus subtilis*, or yeast is used. In order to solve such problems, animal cells are often used as hosts, in which case, the selection of a promoter has a great impact on expression efficiency. Conventional, frequently used promoters for animal cells include SV40 promoter, cytomegalovirus promoter, actin promoter, and the like.

DISCLOSURE OF THE INVENTION

Considering the above state of art, the present invention provides a genomic DNA encoding HM1.24 antigen protein.

The present invention also provides a process for producing HM1.24 antigen protein using animal cells by means of said genomic DNA.

When a useful gene product is to be produced in large quantities using animal cells as a host, conventionally used promoters for animal cells are not always satisfactory in terms of transcription activity, and hence there is a great need for the development of stronger promoters. Thus, it is an object of the present invention to provide a DNA having a stronger promoter activity as a promoter for animal cells and uses thereof.

In order to solve the above problems, the present invention provides a genomic DNA encoding HM1.24 antigen protein, said DNA comprising 4 exon regions encoding the amino acid sequence as set forth in SEQ ID NO: 2. As an example of the above genomic DNA, the present invention provides a genomic DNA having 4 exons encoding the amino acid sequence and 3 introns as set forth in SEQ ID NO: 2.

The present invention also provides a splicing variant of the above genomic DNA. Specific examples include a splicing variant lacking exon 2, a splicing variant lacking exons 2 and 3, and the like.

The present invention also provides a process for producing HM1.24 antigen protein which method comprises culturing animal cells transformed with an expression vector comprising the above genomic DNA.

The present invention further provides a promoter sequence DNA having the nucleotide sequence of the 5'-non-coding region as set forth in SEQ ID NO: 4 or a DNA fragment of said sequence having a promoter activity in animal cells.

The present invention also provides a DNA that hybridizes with the above DNA or a fragment thereof under a stringent condition and that has a promoter activity in animal cells. The above DNA having promoter activity is preferably derived from animal cells, in particular mammalian cells.

The present invention also provides a DNA that has been modified by the deletion, addition and/or substitution with other nucleotides, of one or a plurality of nucleotides in the nucleotide sequence of the 5'-non-coding region as set forth in SEQ ID NO: 4 and that has a promoter activity in animal cells.

The present invention also provides a recombinant DNA wherein a useful gene is operably linked to the above DNA having a promoter activity. As the above useful genes, there can be mentioned, for example, nucleic acids selected from the group consisting of nucleic acids encoding useful proteins, antisense DNA, antisense RNA, nucleic acids encoding decoys, and ribozyme.

The present invention also provides a vector comprising the above recombinant DNA. The vector is a plasmid vector or a virus vector.

The present invention also provides animal cells into which the above recombinant DNA has been introduced.

The present invention also provides animal cells that have been transformed with the above vector.

The present invention also provides an animal having the above animal cells.

The present invention also provides a method of expressing a useful gene which method comprises culturing animal cells into which the above recombinant DNA has been introduced.

The present invention also a process for producing a useful protein which process comprises culturing animal cells transformed with an expression vector comprising a nucleic acid encoding a useful protein operably linked to the above DNA having a promoter activity.

BRIEF DESCRIPTION OF THE DRAWINGS

FIG. 1 is a drawing that shows the nucleotide sequence of cDNA (SEQ ID NO: 1) encoding HM1.24 antigen protein and the corresponding amino acid sequence (SEQ ID NO: 3). The underlined part shows a N-type sugar chain binding motif.

FIG. 2 is a drawing that shows the nucleotide sequence of Cdna (SEQ ID NO: 1) encoding HM1.24 antigen protein and the corresponding amino acid sequence (SEQ ID NO: 3).

FIG. 7 is a drawing that shows the nucleotide sequence (SEQ ID NO: 4) of the 5'-untranslated region comprising the promoter region of the HM1.24 antigen protein gene. Each transcription factor binding motif has been underlined.

FIG. 8 is a drawing that shows the nucleotide sequence (SEQ ID NO: 4) of the 5'-untranslated region comprising the promoter region of the HM1.24 antigen protein gene. Each transcription factor binding motif has been underlined, the TATA-like sequence has been boxed, the transcription initiation point is represented by an arrow, and the region encoding 7 amino acids at the N-terminal of the protein is represented by the one-letter code of amino acids (SEQ ID NO: 21).

FIG. 11 is a drawing that shows a restriction map of genomic DNA (SEQ ID NO: 2) encoding HM1.24 antigen protein and the corresponding amino acid sequence (SEQ ID NO: 3) (upstream side). The arrow shows the transcription initiation point and the underline shows the N-type sugar chain binding motif.

FIG. 12 is a drawing that shows the nucleotide sequence of genomic DNA (SEQ ID NO: 2) encoding HM1.24 antigen protein and the corresponding amino acid sequence (SEQ ID NO: 3) (downstream side). The double underline shows the poly A-addition signal.

FIG. 13 is a drawing that shows the nucleotide sequence (SEQ ID NO: 19) of a splicing variant of human HM1.24 antigen protein and the corresponding amino acid sequence (SEQ ID NO: 20). The underlined part shows where the amino acid sequence is different from that of human HM1.24 antigen protein.

FIG. 14 is a drawing that shows the nucleotide sequence (SEQ ID NO: 33) of the genomic DNA of HM1.24 antigen protein. A genome was present which has mutations, a.fwdarw.g at position 178, g.fwdarw.a at position 262, and t.fwdarw.c at position 323, as well as a deletion of one of 9 a's near position 360. The symbol "*" represents a transcription initiation point. There was also a genome in which 19 bp at positions 93–111 repeat in tandem. The symbol ".fwdarw." shows the position of the sense primer.

FIG. 15 shows the nucleotide sequence of genomic DNA of HM1.24 antigen protein and the corresponding amino acid sequence. There was also a genome in which 8 base pairs at positions 551–558 were deleted. The symbol "←" shows the position of the antisense primer.

FIG. 16 is a drawing that shows the nucleotide sequence (SEQ ID NO: 33) of genomic DNA (intron site) of HM1.24 antigen protein. The .fwdarw. shows the position of the sense primer.

FIG. 17 shows the nucleotide sequence of genomic DNA of HM1.24 antigen protein and the corresponding amino acid sequence. The → shows the sense primer, and the ← indicates the antisense primer.

FIG. 18 shows the nucleotide sequence of genomic DNA of HM1.24 antigen protein and the corresponding amino acid sequence. There was also a genome in which 3 out of 5 c's near position 2315 were deleted. The ← shows the position of the antisense primer.

EMBODIMENT FOR CARRYING OUT THE INVENTION

A genomic gene comprising a genomic DNA and a promoter region of human HM1.24 antigen can be easily amplified by a PCR method using suitable primers. Thus, a genomic DNA of human HM1.24 antigen can be amplified by designing a sense primer that hybridizes to the 5'-end of a genomic DNA sequence as set forth in SEQ ID NO: 2 and an antisense primer that hybridizes to the 3'-end, and then by performing a PCR reaction using a polymerase, such as AmpliTaq (Perkin Elmer), LA-Taq (Takara Shuzo), and the like, and using as a template human genomic DNA prepared according to a standard method. A PCR product can be directly inserted into a cloning vector such as pCRII (Invitrogen) or pGEM-T (Promega).

By introducing a restriction enzyme recognition site into a sense primer or an antisense primer, it can be inserted into a desired vector.

Genomic DNA that contains a promoter region of human HM1.24 antigen can also be amplified by the same method. Thus, a desired DNA fragment can be obtained by designing a sense primer that hybridizes to the 5'-end of the sequence as set forth in SEQ ID NO: 4 and an antisense primer that hybridizes to the 3'-end, and then by amplifying by a PCR reaction using human genomic DNA as a template.

Figure 10:
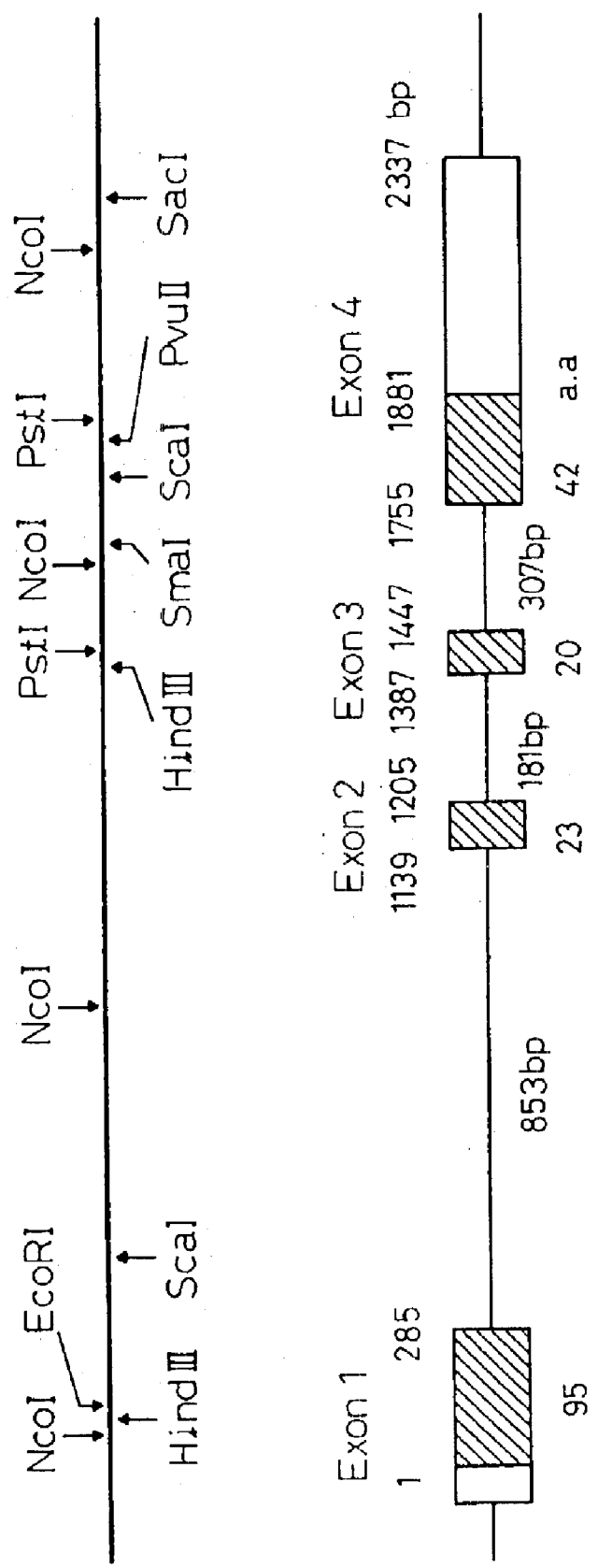
FIG. 10 is a drawing that shows a restriction map of genomic DNA encoding HM1.24 antigen protein and the positions of the corresponding exons and introns.

A genomic DNA encoding HM1.24 antigen protein of the present invention comprises, as shown in FIG. 10, 4 exons and 3 introns linking them, and their specific nucleotide sequences and deduced amino acid sequences of the exon regions are as shown in FIGS. 11 and 12 (SEQ ID NO: 2). Thus, exon 1 encodes from amino acid Met at position 1 to amino acid Val at position 95; exon 2 encodes from amino acid Met at position 96 to amino acid Glu at position 117; exon 3 encodes from amino acid Glu at position 118 to amino acid Arg at position 138; and exon 4 encodes from amino acid Arg at position 139 to amino acid Gln at position 180.

The present invention also provides splicing variants of genomic DNA encoding HM1.24 antigen protein. Splicing variants are those in which at least one, i.e. 1 to 3, of exons 1 to 4 has been removed, for example exon 2 or 3, or both of them are removed.

The present invention also provides splicing variants of genomic DNA encoding HM1.24 antigen protein having a nucleotide sequence of DNA in which the codon corresponding to each amino acid of at exon is out of position because the nucleotide sequence in an exon was deleted due to splicing.

Since the splicing variants have the reading frames of different amino acid sequences, they have amino acid sequences different from that of HM1.24 antigen protein encoded by exons 1 to 4. As an example of such splicing variants, there can be mentioned a splicing variant having the nucleotide sequence and the amino acid sequence as set forth in SEQ ID NO: 17.

A genomic DNA encoding the HM1.24 antigen protein of the present invention can be obtained by cloning a cDNA that encodes HM1.24 antigen protein, then using this cDNA to design a primer oligonucleotide, which is amplified by the PCR method using genomic DNA as a template. In order to clone cDNA, animal cells expressing HM1.24 antigen, for example KPMM2 cells, are cultured, and from the cell culture total RNA is extracted according to a standard method and then mRNA is enriched.

According to the present invention, based on the above mRNA, cDNA is synthesized by a standard method, which is fractionated using a low-melting point agarose gel. Then cDNA having a size of 0.7 kbp or greater is inserted into an expression vector pCOS1 or λExCell vector to prepare a library A which is used for screening by direct expression cloning, i.e. panning, and library B which is used for immunoscreening.

For screening the panning method an expression plasmid that constitutes library A was in introduced into COS-7 cells using electroporation. After culturing, attached cells were scraped off and were contacted to a panning plate coated with anti-HM1.24 antibody to allow the cells expressing HM1.24 to be attached to the plate. Then plasmid DNA was extracted from the cells attached to the plate, amplified in *E. coli*, and used for the subsequent panning. The panning procedure was repeated three times to select clones that express antigen reacting with anti-HM1.24 antibody, and one of the clones was designated as clone P3.19.

Sequencing revealed that clone P3.19 consists of 1,012 bp and contains an open reading frame encoding 180 amino acids. The nucleotide sequence of the cDNA insert in this clone P3.19 and the corresponding amino acid sequence are shown in FIG. 1 and SEQ ID NO: 1. The amino acid sequence alone is shown in SEQ ID NO: 3.

For immunoscreening, on the other hand, a phage constituting library B was cultured together with *E. coli* NM522 on an agar plate, the expression product was transferred to a nitrocellulose filter, and the filter was contacted to an anti-HM1.24 antibody solution. Anti-HM1.24 antibody that was bound to the filter via binding with the expression product was detected with labeled anti-mouse immunoglobulin (Ig) serum.

Figure 3:
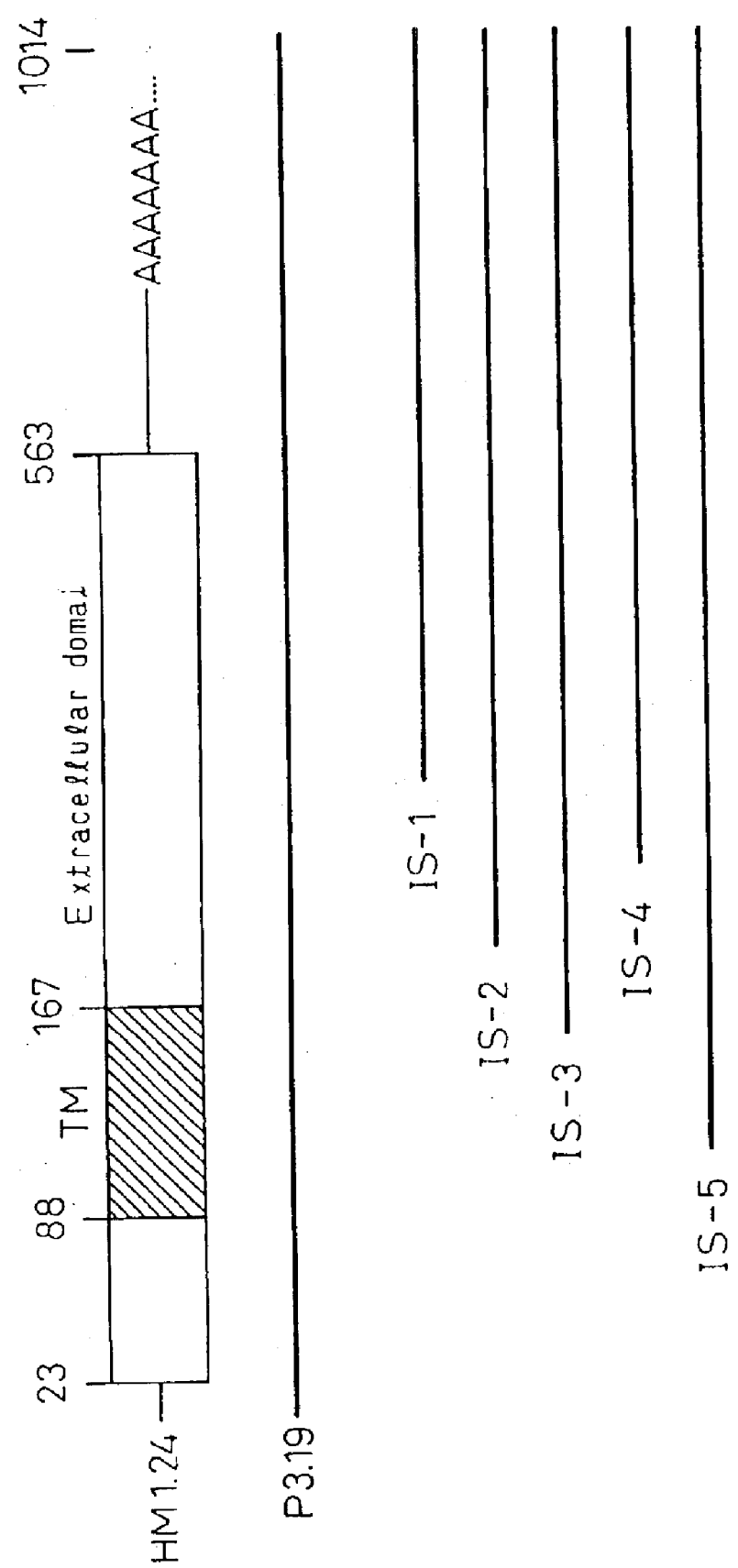
FIG. 3 is a schematic diagram showing a clone P3.19 isolated using the panning method and 5 clones (IS1 to IS5) isolated by the immunoscreening method.

This produced 5 positive clones: IS-1 to IS-5. The nucleotide sequences of these cDNA inserts-were determined and were compared to the nucleotide sequence of the cDNA of the above P3.19. The comparison revealed, as shown in FIG. 3, that any cDNA in clones IS-1 to IS-5 was part of the cDNA of P3.19 and the 5'-end has been deleted in P3.19.

Figure 4:
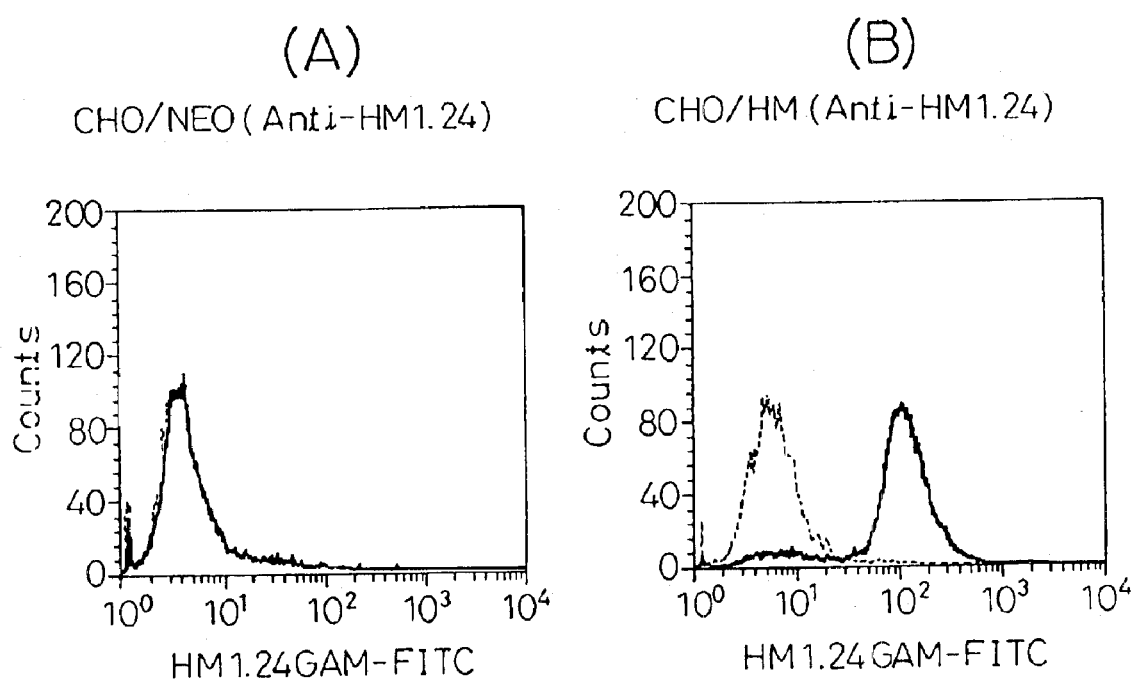
FIG. 4 is a drawing that shows the result of flow cytometry analysis using anti-HM1.24 antibody (A: CHO/NEO, B: CHO/HM). The histogram of anti-HM1.24 antibody is shown by a solid line, and that of the control antibody (UPC10) that showed a matching isotype is shown by a broken line. In the figure, the abscissa refers to fluorescence intensity and the ordinate to cell count.

Then, after P3.19 was introduced into CHO cells to transform the cells, flow cytometry was performed using anti-HM1.24 antibody. The result confirmed, as shown in FIG. 4, that HM1.24 antigen was expressed. Furthermore, as shown in FIG. 4, P3.19 was confirmed to encode HM1.24 antigen by immunoprecipitation as well.

Then, as shown in FIG. 9A, the cDNA sequence was divided into four regions, and primer pairs were designed as shown in FIG. 9B to amplify each part. The genome library prepared according to a standard method was PCR-amplified using the above each pair of primers, which were then ligated together to obtain a full-length genomic DNA.

The result is shown in FIGS. 11 and 12, and SEQ ID NO: 2. As can be seen, the genomic DNA encoding HM1.24 antigen protein has 4 exons and 3 introns linking them. These relationships are schematically shown in FIG. 10, which also shows a restriction map of genomic DNA.

The present invention also relates to a process for producing HM1.24 antigen protein which method comprises culturing animal cells transformed with an expression vector into which the above genomic DNA has been inserted. As animal cells for use in this process, various animal cells, for example, described below with respect to the promoters of the present invention may be used, and cell cultures of humans, mammals other than humans, insects and the like are preferred. For example, HeLa etc. are used as the cell culture of humans; CHO, COS, myeloma, BHK, Vero, etc. are mentioned as the cell cultures of mammals other than humans; and cell cultures of silkworm etc. are mentioned as the cell cultures of insects. As vectors for introducing DNA encoding the HM1.24 antigen protein of the present invention into animal cells, for example phage vectors such as M13 are used.

Culturing of animal cells for producing HM1.24 antigen protein can be performed according to a standard method, and the isolation of HM1.24 antigen protein from the culture can also be performed according to a standard method.

Hybridoma HM1.24 producing mouse anti-HM1.24 monoclonal antibody that specifically recognizes HM1.24 antigen protein has been internationally deposited under the provisions of the Budapest Treaty as FERM BP-5233 on Sep. 14, 1995 with the National Institute of Bioscience and Human Technology, Agency of Industrial Science and Technology, of 1–3, Higashi 1-chome, Tsukuba-shi, Ibaraki pref., Japan.

The promoter of the present invention and the uses thereof will now be explained below.

The word "promoter" as used herein includes, but is not limited to, a region that is located 20–30 base pairs upstream to the transcription initiation point (+1) and that includes a TATA box or a TATA box-like region responsible for directing RNA polymerase to start transcription at a correct position, and, in addition to this region, it may include regions that are required for proteins, other than RNA polymerase, to associate with for adjusting expression. When the term "promoter region" is used in the present invention, it means a region that includes the promoter as used herein.

The words "promoter activity" as used herein means an ability or a function of being ligated to a useful gene downstream to the promoter in a state that enables expression, so that when introduced into a host (animal cell) it can produce either intracellularly or extracellularly a gene product of the useful gene. In general, the presence or absence and/or intensity of a promoter is expressed as the promoter activity by ligating, downstream to the promoter, a gene (reporter gene) encoding an easily quantifiable protein in a state that enables expression, introducing it into a host, and then determining the amount expressed of the protein. Thus, when the expression of gene products of a useful gene were confirmed either intracellularly or extracellularly after the useful gene was ligated downstream to the promoter and introduced into a host, the promoter should have a promoter activity in the host into which the gene was introduced.

The words "animal cells" as used herein includes cells derived from humans, but they are not limited to them as long as the promoter of the present invention has a promoter activity in an animal cell. For example, there can be mentioned mammals other than humans (for example, mice, rats, rabbits, goat, pigs, cattle, horses, dogs, monkeys, and chimpanzees), birds (for example, chickens, turkeys, quails, ducks, and geese), reptiles (for example, snakes, crocodiles, and turtles), amphibians (for example, frogs, salamanders, and newts), fish (for example, scads, mackerel, sea bass, sea breams, sea perch, yellowtails, tuna, salmon, trout, carp, sweetfish, eel, soles, sharks, rays, and sturgeons).

The words "useful genes" as used herein includes, for example, nucleic acids encoding proteins that can be expressed in animal cells, antisense DNA or sense DNA of genes derived from animal cells, nucleic acids encoding decoys that have genes encoding the binding proteins of transcription factors derived from animal cells or sequences of the binding sites of transcription factors or similar sequences, and ribozymes that cleave mRNA derived from animal cells.

As nucleic acids encoding protein that can be expressed in animal cells include, but not limited to, those derived from animals, and as long as they can be expressed in animal cells, those derived from microorganisms such as bacteria, yeasts, actinomycetes, fungi, *Ascomycetes*, and *Basidiomycetes*, or those derived from living organisms such as plants and insects are also included in the useful genes mentioned in this specification.

The words "nucleic acids encoding decoys" as used herein means DNA that have genes encoding the binding proteins of transcription factors derived from animal cells or sequences of the binding sites of transcription factors or similar sequences, which are introduced as "decoys" into cells so as to suppress the action of the transcription factors. The word "ribozymes" as used herein means those that cleave mRNA of specific proteins, and that inhibits the translation of these specific proteins.

Ribozyme can be designed from gene sequences encoding specific proteins and, for a hammerhead type ribozyme, for example, the method as described in FEBS Letter, 228: 228–230 (1988) can be used. In addition to the hammerhead type ribozymes, any type of ribozymes including the hairpin type ribozymes, the delta type ribozymes, and the like that cleave mRNA of these specific proteins and that inhibit the translation of these specific proteins can be included in the ribozyme as used herein.

By ligating a useful gene downstream to a DNA fragment having the promoter activity of the present invention in a state that enables expression, the expression of the useful gene can be enhanced. Thus, useful genes are expressed in animal cells into which recombinant DNA comprising DNA having the promoter activity of the present invention and a useful gene ligated in a state that enables expression has been introduced with or without using a vector. As a vector, a plasmid vectors or a virus vectors is preferably used. When vectors are not used, DNA fragments can be introduced according to the methods described in the literature [Virology, 52: 456 (1973); Molecular and Cellular Biology, 7: 2745 (1987); Journal of the National Cancer Institute, 41: 351 (1968); EMBO Journal, 1: 841 (1982)].

Animal cells having such recombinant DNA fragments of the present invention and animals having such animal cells are also encompassed in the scope of the present invention. As useful genes whose expression can be enhanced according to the present invention, there can be mentioned, as described above, DNA encoding protein, antisense DNA, antisense RNA, polynucleotides encoding a decoy, nucleotide sequences functioning as a decoy, ribozymes, and the like. The present invention also discloses methods of producing proteins of interest, and methods of expressing useful genes using a DNA fragment having the promoter activity of the present invention.

Thus, a process for producing protein is also encompassed in the scope of the present invention wherein said process comprises ligating a nucleic acid encoding protein downstream to DNA having the promoter activity of the present invention in a state that enables expression, culturing an animal cell transformed with a vector containing the recombinant DNA thus obtained, and harvesting said protein from the culture. Similarly, a method of expressing a useful gene comprising ligating a useful gene downstream to DNA having the promoter activity of the present invention in a state that enables expression, introducing the recombinant DNA thus obtained into an animal cell, and culturing, or the method of expressing a useful gene using an animal cell said method comprising transforming an animal cell with a vector containing said recombinant DNA and culturing said animal cell is also encompassed in the scope of the present invention.

DNA having the promoter activity of the present invention is DNA having the nucleotide sequence shown in the 5'-end non-coding region as set forth in SEQ ID NO: 4 or a fragment thereof retaining a promoter activity. The 5'-end non-coding region means the nucleotide sequence up to position 2040 in SEQ ID NO: 4. It is known that a size of 5 nucleotides or greater is required to exhibit a promoter activity in animal cells. Thus, fragments of DNA having the promoter activity of the present invention have a size of at least 5 nucleotides or greater, preferably 30 nucleotides or greater, and more preferably 2000 nucleotides or greater.

The present invention also includes DNA that can hybridize with DNA having the nucleotide sequence as set forth in SEQ ID NO: 4 under a stringent condition and that has a promoter activity. The hybridizing DNA is for example a genomic DNA library derived from natural sources, for example mammals such as humans, mice, rats, and monkeys. As a stringent condition, there may be mentioned for example a low stringent condition. By way of example, a low stringent condition is a washing condition provided by 42° C. in 5×SSC, 0.1% sodium dodecyl sulfate, and 50% formamide. More preferably, a high stringent condition may be mentioned. By way of example, a high stringent condition is a washing condition provided by 60° C. in 0.1×SSC and 0.1% sodium dodecyl sulfate.

The present invention also includes a DNA fragment that has been modified by the deletion, addition, and/or substitution with other bases, of one or a plurality of nucleotides in the nucleotide sequence of the promoter as set forth in SEQ ID NO: 4 and that retains a promoter activity. The degree of modification is in the range of 70% homology to the nucleotide sequence as set forth in SEQ ID NO: 4, preferably a homology of 80% or greater, and more preferably a homology of 90% or greater.

"Homology" as used herein means the degree of identity of residues exhibited by two or more non-complementary nucleotide sequences or amino acid sequences (Gene Cloning 2nd edition, T. A. Brown, Chapman and Hall, 1990). Thus, a homology of 90% means that 90 residues or more out of 100 are identical in two or more sequences.

Now, a process for producing DNA having the promoter activity of the present invention, a fragment and a modified version thereof will be explained below. The DNA having the nucleotide sequence as set forth in SEQ ID NO: 4 was PCR-amplified using a primer AP1 (5'-GTAATACGACTCACTATAGGGC-3') (SEQ ID NO: 5) corresponding to an adapter and the HM1 primer (sequence: 5'-ATC CCC GTC TTC CAT GGG CAC TCT GCA-3' (SEQ ID NO: 6) corresponding to nucleotide Nos. 47–72 of cDNA clone P3.19 cloned by the above-mentioned panning method, and a human genomic DNA library as a template, and then, using the PCR-amplified product as a template, a nested PCR is performed using the AP2 primer (sequence: ACTATAGGGC ACGCGTGGT) (SEQ ID NO: 7) and the HM2 primer (sequence: 5'-ATA GTC ATA CGA AGT AGA TGC CAT CCA G-3' (SEQ ID NO: 8) corresponding to nucleotides 19–40 of clone P3.19 to subclone into a cloning vector pCRII (Invitrogen). By sequencing, DNA having the nucleotide sequence as set forth in SEQ ID NO: 4 was obtained.

A DNA fragment having a promoter can be obtained, for example, in the following manner. A method of digesting a DNA subcloned into the above cloning vector pCRII with restriction enzymes, ScaI, BamHI, PvuII, PstI, etc., a method using an ultrasonication treatment, a chemical synthesis by the phosphoramidite method, a method of preparation using a polymerase chain reaction method etc. can be used. For example, a desired DNA fragment can be easily prepared by preparing a primer as appropriate from the DNA sequence of SEQ ID NO: 4 and then performing a polymerase chain reaction.

A hybridization method that utilizes the nucleotide sequence of the promoter of the present invention may be used to obtain a promoter of the present invention from a gene derived from other cells. In this case, for example, the following method can be used. First, a chromosomal DNA obtained from a gene source of other cells is ligated into a plasmid or a phage vector and then introduced into a host according to a standard method to construct a library. The library is cultured on a plate, and colonies or plaques grown are transferred to a nitrocellulose or a nylon membrane, which is subjected to denaturation to immobilize DNA onto the membrane. The membrane is incubated in a solution containing a probe (as the probe, a DNA fragment as set forth in SEQ ID NO: 4 or a portion thereof) previously labeled with $^{32}P$ etc. to form a hybrid between the DNA on the membrane and the probe. For example, a DNA-immobilized membrane is subjected to hybridization with a probe in a solution containing 6×SSC, 1% sodium dodecyl sulfate (SDS), 100 μg/ml salmon sperm DNA, 5× Denhardt's at 65° C. for 20 hours. After hybridization, non-specific adsorption is washed off, and autoradiography etc. is performed to identify clones that hybridized with the probe. The procedure is repeated until a single clone that formed a hybrid is obtained. Into a clone thus obtained, DNA encoding a desired promoter should be inserted.

The above promoter that has been modified by the deletion, addition, and/or substitution of nucleotides can be prepared by, for example, conventionally known methods such as site-directed mutagenesis, or a PCR method.

The gene obtained is sequenced for its nucleotide sequence, for example, in the following manner to confirm the gene obtained is a promoter of interest. For the determination of the nucleotide sequence, in the case of a clone obtained by hybridization, the transformant is cultured in a test tube if it is E. coli, and a plasmid is extracted therefrom according to a standard method. This is cleaved with a restriction enzyme to extract an inserted fragment, which is subcloned into M13 phage vector etc., and the nucleotide sequence is determined by the dideoxy method or the like.

When the transformant is a phage, essentially similar steps can be employed to determine the nucleotide sequence. Basic procedures from culturing to nucleotide sequence determination are carried out as described in, for example, Molecular Cloning: A laboratory Manual, Second edition, T. Maniatis, Chapter One, pp. 90–104, Cold Spring Harbor Laboratory, 1989.

Whether the obtained gene is a promoter of interest or not can be determined by comparing the determined nucleotide sequence with the promoter of the present invention and estimating from its homology. If the obtained gene is thought not to contain an entire promoter, a synthetic DNA primer is constructed based on the obtained gene, missing regions are amplified by PCR, and using the obtained gene fragment as a probe DNA libraries or cDNA libraries are screened so that the nucleotide sequence of the entire conding region of the promoter that hybridizes to the promoter of the present invention can be determined.

The method of expressing useful genes of the present invention is characterized in that a DNA fragment obtained by ligating, in a state that enables expression, a useful gene downstream to the promoter of the present invention thus obtained is introduced into an animal cell and the resulting cell is cultured. In order to ligate, in a state that enables expression, a useful gene downstream to the DNA fragment of the promoter of the present invention prepared as above, the DNA ligase method or the homopolymer method can be used.

If DNA ligase is used for ligating of the two, they are ligated by digesting with restriction enzymes and, if they have the same restriction enzyme site, then both the DNA fragments are mixed in a reaction buffer as described in Molecular Cloning: A laboratory Manual, Second edition, T. Maniatis et al. ed., Chapter One, pp. 62, Cold Spring Harbor Laboratory, 1989, and adding DNA ligase thereto or, if the they do not share the same restriction enzyme site, the ends are blunt-ended with T4 DNA polymerase (manufactured by Takara), and then treated with DNA ligase as described above.

On the other hand, when the homopolymer method is used, ligating is effected by attaching a poly G chain to the 3'-end of a vector linearized with a restriction enzyme using terminal deoxyribonucleotidyl transferase and dGTP, attaching similarly a poly C chain to the 3'-end of the insert DNA, and then annealing these poly G chain and poly C chain by, for example, the calcium chloride method for introduction into E. coli [Proc. Natl. Acad. Sci. U.S.A., 75: 3727 (1978)].

The useful genes of interest that can be used in the present invention includes, but not limited to, the interleukin 1–12 gene, the interferon α, β, γ genes, the tumor necrosis factor gene, the colony stimulating factor gene, the erythropoietin gene, the transforming growth factor-β gene, the immunoglobulin gene, the tissue plasminogen activator gene, the urokinase gene, the horseradish peroxidase gene, and the like.

There can be mentioned for example, genes of superoxide dismutase, tumor necrosis factor, insulin, calcitonin, somatostatin, secretin, growth hormone, endorphine, viral protein, amylase, lipase, alcohol dehydrogenase, and the like.

The DNA fragment obtained as above in which the DNA fragment of the present invention and a useful gene is ligated can be integrated into an appropriate vector to obtain a plasmid for gene expression. Examples of such vectors include pTM [Nucleic Acids Research, 10: 6715 (1982)], cos202 [The EMBO Journal, 6: 355 (1987)], p91203 (B)

[Science, 228: 810 (1985)], BCMGSNeo [Journal of Experimental Medicine, 172: 969 (1990)], and the like.

The plasmid thus obtained for gene expression can be introduced into a suitable host by the calcium phosphate method [Molecular and Cellular Biology, 7: 2745 (1987)], the electroporation method [Proc. Natl. Acad. Sci. U.S.A., 81: 7161 (1984)], the DEAE-dextran method [Methods in Nucleic Acids Research, page 283, Column et al., ed., CRC Press, issued in 1991], the liposome method [BioTechniques, 6: 682 (1989)], and the like.

Examples of such host cells include COS cells, HeLa cells, CHO cells, BHK-21 cells, and the like. By culturing the resulting transformed cells in a suitable medium, the useful gene product of interest can be obtained in an efficient manner.

EXAMPLES

The present invention will now be explained in more detail with reference to the following working Examples and Reference Examples.

Reference Example 1

Cloning of cDNA Encoding HM1.24 Antigen Protein

1) Cell Lines

Human multiple myeloma cell lines RPMI8226 and U266 were cultured in a RPMI1640 medium (GIBCO-BRL) supplemented with 10% fetal bovine serum (FBS), and a human multiple myeloma cell line KPMM2 (Japanese Unexamined Patent Publication (Kokai) No. 7-236475) was cultured in a RPMI1640 medium (GIBCO-BRL) supplemented with 20% fetal bovine serum.

2) Construction of cDNA Library

Total RNA was isolated from $1 \times 10^8$ KPMM2 cells by a guanidine thiocyanate/cesium chloride method, and mRNA was purified using the Fast Track mRNA Isolation Kit (Invitrogen). After synthesizing cDNA from 10 μg of mRNA using NotI/oligo-$dT_{18}$ primer (Time Saver cDNA Synthesis Kit; Pharmacia Biotech), an EcoRI adapter was ligated thereto. A cDNA larger than 0.7 kbp was fractionated using 1.0% low-melting point agarose gel (Sigma), and digested with NotI. It was then inserted into the EcoRI/NotI site of a pCOS1 expression vector or a λExCell vector (Pharmacia Biotech) to prepare a library (library A) for use in direct expression cloning (screening by panning) and a library (library B) for use in immunoscreening, respectively.

The pCOS1 expression vector was constructed from HEF-PMh-gγl (see WO92–19759) by deleting the contained gene with EcoRI and SmaI digestion, and then by ligating the EcoRI-NotI-BamHI Adaptor (Takara Shuzo).

3) Panning

Library A was introduced into COS-7 cells by the electroporation method. Thus, 20 μg of a plasmid DNA (containing $5 \times 10^5$ independent clones) was mixed with 0.8 ml of cells ($1 \times 10^7$ cells/ml in PBS), and the mixture was subjected to electroporation under a condition of 1.5 kV and 25 μFD capacity using the Gene Pulser (Bio-Rad). After being allowed to stand at room temperature for 10 minutes, the cells were suspended in a DMEM (manufactured by GIBCO-BRL) containing 10% FBS, divided into four 100 mm culture dishes, and cultured at 37° C. for 72 hours.

After culturing, the cells were washed with a phosphate saline buffer (PBS), and were scraped off by adding PBS containing 5 mM EDTA to adjust the cell suspension to 1 to $2 \times 10^6$ cells/ml in PBS containing 5% FBS and 0.02% $NaN_3$. The cells were then allowed to stand on a panning plate (see below) coated with anti-HM1.24 antibody for 2 hours, and the plate was gently washed three times with 3 ml of PBS containing 5% FBS and 0.02% $NaN_3$. After washing, plasmid DNA was recovered from the cells bound to the plate using Hirt's solution (Hitt J., Mol. Biol. 26: 365–369, 1983) (0.6% SDS, 10 mM EDTA). The recovered plasmid DNA was amplified in E. coli and used for the following panning.

A panning plate was prepared as follows. Three milliliters of an anti-HM1.24 antibody solution (10 μg/ml in 50 mM Tris-HCl, pH 9.5) was added to a cell culture dish (Falcon) with a diameter of 60 mm and was incubated at room temperature for 2 hours. After washing three times in 0.15 M NaCl, 3 ml of PBS containing 5% FBS, 1 mM EDTA, and 0.02% $NaN_3$ was added to the dish. After blocking by allowing to stand at room temperature for 2 hours, the panning plate was stored at −20° C. until use.

By repeating panning three times using a plasmid library (library A) containing $5 \times 10^5$ clones as a starting material, a plasmid DNA having an about 0.9 kbp cDNA as an insert was concentrated. Using a Dye. Terminator Cycle Sequencing Kit (manufactured by Applied Biosystems), the nucleotide sequence was determined using the 373A or 377DNA Sequencer (Applied Biosystems). The result revealed that clone P3.19 comprises 1,012 bp cDNA and has an open reading frame (23-549) encoding 180 amino acids (FIGS. 1 and 2) (SEQ ID NO: 1). The amino acid sequence deduced from the cDNA had a structure characteristic to type II membrane proteins and had two N-type sugar chain binding sites.

4) Immunoscreening

Library B was subjected to immunoscreening using anti-HM1.24 antibody. Thus, a phage library containing $1.5 \times 10^5$ independent clones was layered on agar together with E. coli NM522 (Pharmacia Biotech) and was cultured at 42° C. for 3.5 hours. After culturing, a nitrocellulose filter (Schleicher & Schuell) pretreated with 10 mM IPTG was layered on the plate, and was further cultured at 37° C. for 3 hours. After the filter was washed with 0.05% (v/v) Tween 20-added TBS (20 mM Tris-HCl, pH 7.4, 150 mM NaCl), 1% (w/v) BSA-added TBS was added thereto, and was blocked by incubating at room temperature for 1 hour.

After blocking, an anti-HM1.24 antibody solution (a 10 μg/ml blocking buffer) was added, incubated at room temperature for 1 hour, and 5,000-fold diluted alkaline phosphatase-conjugated anti-mouse Ig antiserum (picoBlue Immunoscreening kit; Stratagene) was added, which was further incubated at room temperature for 1 hour. Spots that reacted with the antibody were allowed to develop color with a developing solution (100 mM Tris-HCl, pH 9.5, 100 mM NaCl, 5 mM $MgCl_2$) containing 0.3 mg/ml nitroblue tetrazolium and 0.15 mg/ml 5-bromo-4-chloro-3-indolyl phosphate.

By immunoscreening, five positive clones were isolated, all of which were consistent with the partial sequence of P3.19 (FIG. 3). Homology search of them revealed that P3.19 is identical with the DNA sequence of BST-2 (Ishikawa J. et al., Genomics, 26: 527–534, 1995) expressed on the bone marrow or synovial stromal cells. The same molecule was obtained from two types of screening, which strongly suggested that the membrane protein encoded by P3.19 is the HM1.24 antigen molecule.

E. coli having the plasmid pRS38-pUC19 in which DNA encoding a human protein having the same sequence as the above-mentioned human HM1.24 antigen protein has been inserted in between the XbaI sites of pUC vector was designated as *Escherichia coli* DH5α (pRS38-pUC19) and was internationally deposited under the provisions of the Budapest Treaty on Oct. 5, 1993 with the National Institute of Bioscience and Human Technology, Agency of Industrial Science and Technology, of 1–3, Higashi 1-chome, Tsukubashi, Ibaraki pref., Japan, under an accession No. FERM BP-4434.

5) FACS Analysis

Furthermore, in order to confirm that the protein encoded by p3.19 indeed binds to anti-HM1.24 antibody, a CHO transformant cell line in which P3.19 was introduced was established. Thus, after the P3.19 clone was introduced into CHO cells by the electroporation method, it was cultured in the presence of 500 µg/ml G418 (GIBCO-BRL) to obtain a CHO cell line that expresses HM1.24 antigen.

The cultured cells ($1 \times 10^6$) were suspended to the FACS buffer (PBS (−)/2% FCS/0.1% $NaN_3$), HM1.24 antibody was added thereto, which was reacted on ice for 30 minutes. After washing in the FACS buffer, it was resuspended in a GAM-FITC solution (25 µg/ml in the FACS buffer; Becton Dickinson), and was further reacted on ice for 30 minutes. After washing twice with the FACS buffer, it was resuspended in 600 µl of the FACS buffer for measurement by the FACScan (Becton Dickinson).

As a negative control, UPC10 was used.

As result of FACS analysis, CHO cells in which P3.19 was introduced were shown to react strongly with anti-HM1.24 antibody, whereas no binding was observed in CHO cells (CHO/NEO) in which the control expression vector was introduced (FIG. 17). It was confirmed therefore that the protein encoded by P3.19 binds to anti-HM1.24 antibody.

6) Immunoprecipitation

After washing the cells twice in PBS (−), they were destructed by ultrasonication in the cell lysate buffer method (50 mM sodium borate, 150 mM NaCl, 0.5% sodium deoxycholate, 1% Nonidet P-40, 0.1 mg/ml phenylmethylsulfonyl fluoride, protease inhibitor cocktail [Boehringer Mannheim]) to obtain a soluble fraction. The soluble fraction was added to anti-HM1.24 antibody-conjugated Sepharose 4B beads. After centrifugation, the precipitate was separated on SDS-PAGE (12% gel), which was transferred onto a PVDF membrane. The PVDF membrane was reacted with anti-HM1.24 antibody, and then with POD-anti-mouse IgG, and detected using the ECL kit (Amersham).

Figure 5:
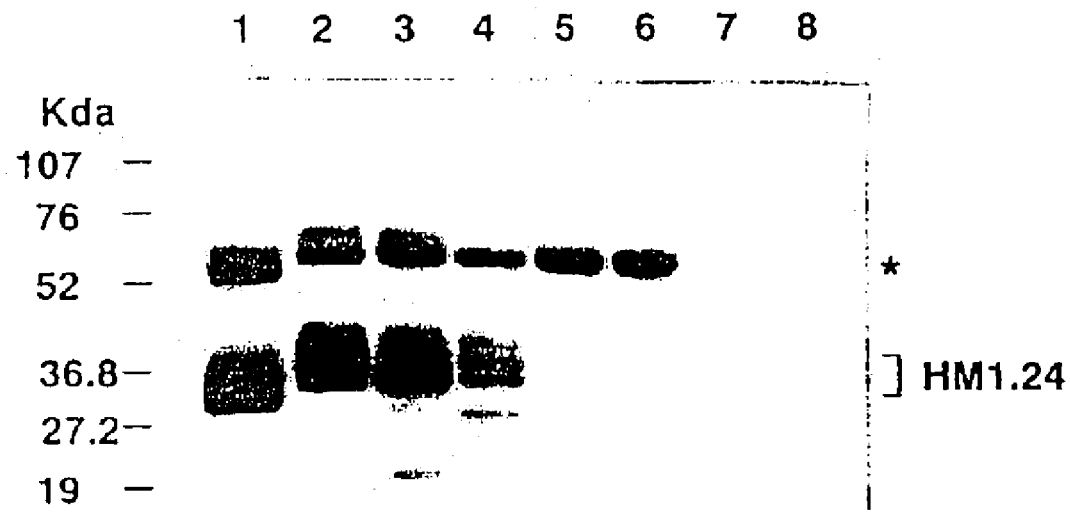
FIG. 5 is a photograph in which the expression of HM1.24 antigen in each cell line and HM1.24 antigen-expressing CHO cells was detected by the immunoprecipitation/Western blotting method using anti-HM1.24 antibody. After immunoprecipitation using the anti-HM1.24 antibody-bound Sepharose 4B (lanes 1–6) or unbound Sepharose 4B (lanes 7 and 8), Western blotting was carried out using anti-HM1.24 antibody to detect HM1.24 antigen (shown on the right). (*: anti-HM1.24 antibody H chain).

Each of myeloma cell lines KPMM2, RPMI8226, and U266 strongly expressed HM1.24 antigen, and the immunoprecipitation of the cell lysates thereof with anti-HM1.24 antibody allowed the specific detection of protein with a molecular weight of about 29 to 33 kDa (FIG. 5). In a similar experiment for CHO cell lines (CHO/HM) in which P3.19 was introduced, immunoprecipitants were confirmed in the CHO/HM cells as for the myeloma cell lines (FIG. 5, lane 4). Such immunoprecipitants could not be observed in the control cells (CHO/NEO) in which the expression vector pCOS1 was only introduced (FIG. 5, lane 5).

P3.19 encodes a protein having an estimated molecular weight of 19.8 kDa comprising 180 amino acids (FIG. 1) and has two N-type sugar chain binding motifs (FIG. 1). Thus, it suggested that the presence of substances having different molecular weights observed by immunoprecipitation was due to differences in the modification of N-type sugar chains. In fact, the immunoprecipitants were confirmed to bind to several lectins.

Reference Example 2

Preparation of Hybridomas that Produce Mouse Anti-HM1.24 Monoclonal Antibody

In accordance with the method of Goto, T. et al., Blood (1994) 84, 1992–1930, hybridomas that produce mouse anti-HM1.24 monoclonal antibody were prepared.

A plasma cell line KPC-32 ($1 \times 10^7$) derived from the bone marrow of a human patient with multiple myeloma (Goto, T. et al., Jpn. J. Clin. Hematol. (1991) 32, 1400) was injected to the abdominal cavity of a BALB/c mouse (bred by Charles River) twice every six weeks.

Three days prior to sacrificing the animal, $1.5 \times 10^6$ KPC-32 was injected to the spleen of the mouse in order to further enhance the antibody-producing ability of the mouse (Goto, T. et al., Tokushima J. Exp. Med. (1990) 37, 89). After sacrificing the animal, the spleen was extracted and the extracted organ was subjected to cell fusion with the myeloma cell SP2/0-according to the method of Groth, de St. & Schreidegger (Cancer Research (1981) 41, 3465).

By Cell ELISA (Posner, M. R. et al., J. Immunol. Methods (1982) 48, 23) using KPC-32, a culture supernatant of a hybridoma was screened for antibody. $5 \times 10^4$ KPC-32 was suspended in 50 ml of PBS and then was aliquoted to a 96-well plate (U-bottomed, Corning, manufactured by Iwaki), which was then air-dried at 37° C. overnight. After blocking with PBS containing 1% bovine serum albumin (BSA), the culture supernatant of the hybridoma was added thereto and incubated at 4° C. for 2 hours. Then, peroxidase-labeled anti-mouse IgG goat antibody (manufactured by zymed) was reacted at 4° C. for 1 hour. After washing, o-phenylene diamine solution substrate solution (manufactured by Sumitomo Bakelite) was reacted at room temperature for 30 minutes.

Reaction was stopped by adding 2 N sulfuric acid and the absorbance was measured at 492 nm using the ELISA reader (manufactured by Bio-Rad). In order to remove the hybridomas that produce antibodies against human immunoglobulin, a culture supernatant of positive hybridomas had previously been adsorbed to human serum and the reactivity to other cell lines was screened by ELISA. Positive hybridomas were selected, and their reactivity to various cells was investigated by flow cytometry. The last selected hybridoma clone was cloned twice and injected to the abdominal cavity of a pristane-treated BALB/c mouse. The ascites was obtained from the mouse.

Monoclonal antibody was purified from the ascites of the mouse by ammonium sulfate precipitation and a Protein A affinity chromatography kit (Ampure Pa., manufactured by Amersham). The purified antibody was labeled with FITC using the Quick Tag FITC biding kit (manufactured by Boehringer Mannheim).

As a result, monoclonal antibodies produced by 30 hybridoma clones reacted with KPC-32 and RPMI 8226. After cloning, the reactivity of the culture supernatants 2.0 of these hybridomas with other cell lines or peripheral blood mononuclear cells was investigated.

Of them, 3 clones were monoclonal antibodies that specifically reacted with the plasma cell. From the 3 clones, a hybridoma clone that was most useful for flow cytometry analysis and had a CDC activity to RPMI 8226 was selected and designated as HM1.24. The subclass of the monoclonal antibody produced by this hybridoma was determined by an ELISA using a subclass-specific anti-mouse rabbit antibody (manufactured by Zymed). Anti-HM1.24 antibody had a subclass of IgG2a κ. The hybridoma HM1.24 that produces anti-HM1.24 antibody was internationally deposited under the provisions of the Budapest Treaty as FERM BP-5233 on Sep. 14, 1995 with the National Institute of Bioscience and Human Technology, Agency of Industrial Science and Technology, of 1–3, Higashi 1-chome, Tsukuba-shi, Ibaraki pref., Japan.

Example 1

Cloning of the Promoter Region of HM1.24 Antigen Gene

Since HM1.24 antigen was strongly expressed in all the myeloma cells analyzed so far, it is very likely that the expression of HM1.24 antigen is deeply involved in physiological characteristics of multiple myeloma. Thus, the elucidation of the mechanism of HM1.24 antigen expression is an important challenge, and the inventors have clarified the gene structure of the promoter region.

The promoter region of the HM1.24 antigen gene was isolated using the PromoterFinder DNA Walking kit (Clontech). From the nucleotide sequence of the 5'-end of clone P3.19 isolated by Panning, two PCR primers were designed: HM1 (5'-ATC CCC GTC TTC CAT GGG CAC TCT GCA-3') (SEQ ID NO: 6) and HM2 (5'-ATA GTC ATA CGA AGT AGA TGC CAT CCA G-3') (SEQ ID NO: 8). The first PCR was performed using primer AP1 (attached to the kit) corresponding to the adapter and the HM1 primer according to the instruction manual attached to the kit, and then the PCR product was subjected to a nested PCR using the AP2 primer (attached to the kit) and the HM2 primer. After the final PCR product was purified, it was subcloned into the pCRII cloning vector (Invitrogen).

Figure 6:
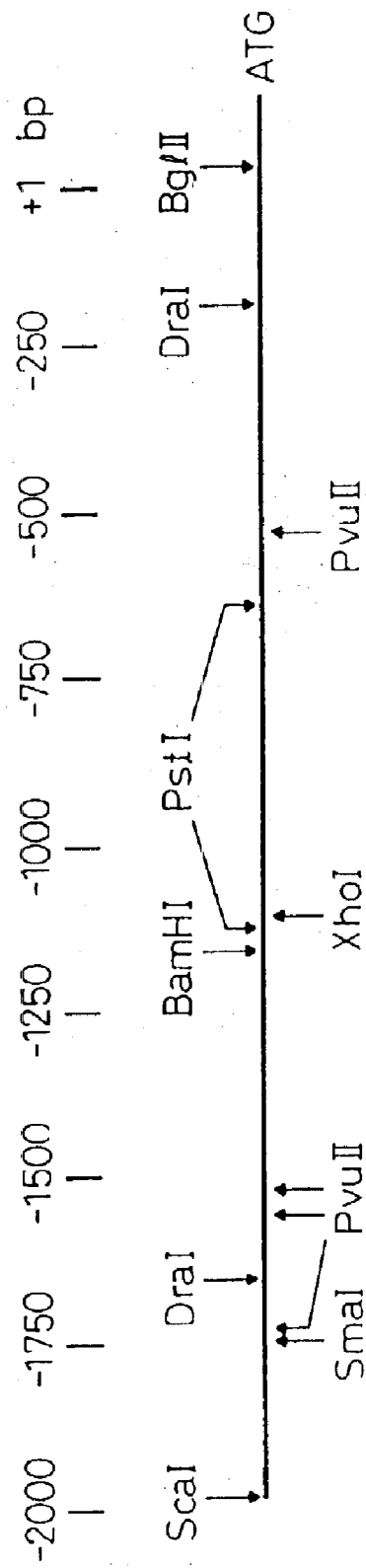
FIG. 6 is a drawing that shows a restriction map of the 5'-untranslated region comprising the promoter region of the HM1.24 antigen protein gene.

The promoter region gene was simply isolated by the PCR method. Thus, PCR products of about 2.0 kb, 0.7 kb, and 0.3 kb were specifically amplified from the EcoRV, PvuII, and DraI libraries (Promoter Finder Kit; Clontech), respectively. They were demonstrated to be derived from the same genomic DNA based on the cleavage patterns with restriction enzymes (FIG. 6). As a result of sequencing the nucleotide sequences, gene sequence of cDNA from 5'-end to 1959 bp upstream was determined (FIGS. 7 and 8) (SEQ ID NO: 4). By a binding motif search of known transcription factors, the presence of transcription controlling elements of AP-2, Sp1, NF-IL6, NF-κB, STAT3 or ISGF3, and the like was observed, suggesting the possibility that the expression is controlled by the stimulation by inflammatory cytokeines such as IL-6 or IFN-α.

IL-6 is known to serve as a growth factor of myeloma cells, and therefore it was strongly suggested that NF-IL6 and STAT3 that are transcription factors acting downstream of IL-6 are involved in the expression control of HM1.24 antigen in myeloma cells (FIGS. 7 and 8). The transcription initiation point was estimated nucleotide on the nucleotide sequence of PCR products amplified using the CapSwitch oligonucleotide (CapFnder Kit; Clonetech), and at 27 positions upstream thereof a TATA box-like sequence (TAATAAA) was observed (FIGS. 7 and 8).

Example 2

Cloning of Genomic DNA for HM1.24 Antigen

Genomic DNA for HM1.24 antigen was amplified from human genomic DNA (Clontech) prepared from a human genomic DNA library (Promoter Finder DNA walking kit; Clontech) or peripheral blood using each PCR primer shown in FIG. 9. After purification, PCR products were each subcloned into the pCRII vector and the nucleotide sequence was determined.

Figure 9:
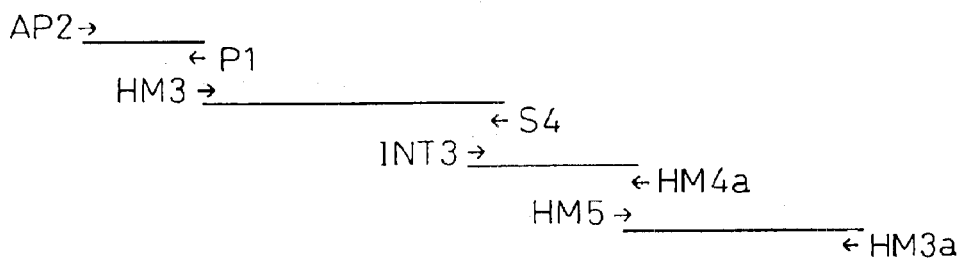
In FIG. 9, (A) shows the position of a primer corresponding to the genonie encoding HM1.24 antigen protein, and (B) shows the base sequence (SEQ ID NOs: 9–16) of each primer.

Genomic DNA encoding HM1.24 antigen was divided into four fragments, which were amplified from human genomic DNA prepared from a human genomic DNA library (Promoter Finder kit; Clontech) or human peripheral blood (FIG. 9). After confirming their nucleotide sequences, they were compared to the nucleotide sequence of HM1.24 antigen cDNA with a result that the HM1.24 antigen gene is composed of four exons and three introns of 850 bp, 183 bp, and 307 bp (FIG. 10).

However, from the human genomic DNA library prepared from the human placenta tissue, a gene consisting of 3 exons lacking intron 3 was only amplified, suggesting the presence of a genomic gene having a different exon/intron structure. In any structure, two N-type sugar chain binding sites and three cysteine residues present in the extracellular region of HM1.24 antigen were all present in exon I (FIGS. 11 and 12) (SEQ ID NO: 2).

Example 3

Confirmation of HM1.24 Antigen Splicing Variants

In order to confirm the presence of splicing variants of HM1.24 antigen, HM1.24 antigen cDNA was amplified by the PCR method using as a template cDNA prepared from a human myeloma cell line KPMM2 according to the method described above. The sense primer BST2-N (SEQ ID NO: 17; ATG GCA TCT ACT TCG TAT GAC) used in the PCR corresponds to bases 10 to 30 of P3.19 (SEQ ID NO: 1), isolated herein, and the antisense primer S3 (SEQ ID NO: 18; AAC CGT GTT GCC CCA TGA) corresponds to bases 641–658 of P3.19.

PCR-amplified products were subcloned into a cloning vector pCRII (Invtrogen) and from the resulting independent clones, plasmid DNA was recovered, with a result that two inserts having different sizes of about 650 bp and about 550 bp were observed. After the determination of each nucleotide sequence, it was found that the insert of about 650 bp had the sequence identical with that of P3.19 whereas the insert of about 550 bp had a deletion corresponding to bases 294 to 422 of P3.19 (SEQ ID NO: 19). The region in which the deletion was observed corresponds to exons 2 and 3 of human HM1.24 antigen genomic DNA, indicating the presence of variants due to different splicing.

Example 4

Analysis of Polymorphism of HM1.24 Gene

In connection with polymorphism found in the HM1.24 gene, its relationship to multiple myeloma was investigated. The peripheral blood samples of normal healthy humans were supplied as the buffy coat of donated blood samples from Japan Red Cross Tokushima Blood Center. For patients with myeloma, the peripheral blood or bone marrow fluid was collected from patients in Tokushima University First Internal Medicine Hospital or affiliated hospitals. Blood samples were subjected to the Ficoll-Conrey density centrifugation to separate mononuclear cells. Myeloma cell lines were cultured in a RPMI1640 medium (GIBCO-BRL, Rockville, Md., U.S.A.) containing 10% fetal bovine serum at 37° C. in a 5% $CO_2$ incubator. The peripheral blood mononuclear cells or the myeloma cell lines were treated with the DNAzol reagent (GIBCO-BRL) according to the protocol to extract genomic DNA from the cells.

The nucleotide sequence was determined by the PCR-direct sequencing method. 5'-promoter region was amplified by PCR (30 cycles of 94° C. for 1 minute, 55° C. for 1 minute, and 72° C. for 1 minute) with ampliTaq DNA polymerase (Perkin Elmer, Chiba) using primer 6S (TCCATAGTCCCCTCGGTGG) (SEQ ID NO: 22) and BST2B (ATAGTCATACGAAGTAGATGCCATCCAG) (SEQ ID NO: 23). The HM coding region was amplified by PCR with LA Taq DNA Polymerase (Takara Shuzo, Otsu) using primer HMP2K (AAAGGTACCAGCTGTCTTTCTGTCTGTC) (SEQ ID NO: 24) and BST2-R4 (GTGCTCTCCCCGCTAACC) (SEQ ID NO: 25). With the reaction mixture as a template, PCR was further performed with Ex Taq DNA polymerase (Takara Shuzo) using primer 8S (GGACGTTTCCTATGCTAA) (SEQ ID NO:26) and BST2-R1 (AAAGCGGCCGCTCATCACTGCAGCAGAGCGCTGAG) (SEQ ID NO: 27)).

The reaction mixture was purified by the QIA Quick PCR Purification Kit (QIAGEN, Tokyo), and reacted with the resulting PCR fragment as a template, using, as a primer, 6S or BST2B for the 5'-promoter region, and 8S, HMINTIF (AGGGGAACTCACCAGACC) (SEQ ID NO: 28), HMEX2F (ATGGCCCTAATGGCTTCC) (SEQ ID NO: 29), HMEX3F (CATTAAACCATAAGCTTCAGG) (SEQ ID NO: 30), HMEX2R (CCCTCAAGCTCCTCCACT) (SEQ ID NO: 31), or BST2-R1 for the HM coding region by the BigDye Terminator Cycle Sequencing Kit (Perkin Elmer). The nucleotide sequence was determined using the ABI3777 DNA Sequencer (Perkin Elmer). The frequency of 8 base pair deletion in the vicinity of 20 base pairs upstream to the initiation codon of the HM1.24 gene was detected by PCR. Thus, PCR (30 cycles of 94° C. for 1 minute, 55° C. for 1 minute, and 72° C. for 1 minute) was performed with ampliTaq DNA polymerase (Perkin Elmer, Chiba) using primers 8S and BST-R3 (GACGGATCCTAAAGCTTACAGCGCTTATC) (SEQ ID NO: 32). The reaction mixture was electrophoresed on a 4% agarose gel and detected by ethidiumbromide staining.

Polymorphism of the 5'-Promoter Region of the HM1.24 Gene

For samples from normal healthy humans and patients, the nucleotide sequence of the 5'-promoter region of the HM1.24 gene was determined. The result is shown in FIGS. 14–18 (SEQ ID NO: 33). There were samples for which nucleotide substitution in the underlined 187, 262, and 323 in FIG. 14, and deletions near 360 in FIG. 14 and near 555 in FIG. 15 were observed, and there was a sample for which the region of 366 to 558 could not be decoded. When the sequence described in FIGS. 14 to 18 (SEQ ID NO: 33) was termed as type A, and the mutation type having the above nucleotide substitution/deletion as type B, the sample for which the region of 366 to 558 could not be decoded is thought to be a heterozygote (AB) of A and B, and the sample that could be decoded as type A or B is thought to be a homozygote (AA) of A or a homozygote (BB) of B. In addition to the above polymorphism, it was clarified that 19 bp was inserted at tandem at the double-underlined region in a myeloma cell line HS-sultan (type M).

Polymorphism of the HM1.24 Gene

For the genomic gene region of cell lines of type AA (U266, HS-sultan) and two samples of type BB from normal healthy humans, the nucleotide sequence was determined. As a result, it was found that 3 bases of c were missing near 2315 of intron 3 in the sequence of type B, whereas no mutation was observed in the coding region.

Gene Frequency of Type A and Type B

Polymorphism and disease sensitivity were investigated. When 8-base deletion was detected by PCR near 20 base pairs upstream to the initiation codon of the HM1.24 gene, there was no difference in frequency of polymorphism between 94 cases of normal healthy humans and 46 cases of patients with myeloma (Table 1). In both the normal healthy humans and the patients with myeloma, type A gene was dominant as the gene distribution was about A:B=2:1. For cell lines, there was a bias to type A with 9 cases out of 11 being type AA.

No relationships were observed between the polymorphism of the HM1.24 promoter region and sensitivity to myeloma diseases.

TABLE 1

| | Frequency of polymorphism | | | |
|---|---|---|---|---|
| | AA | AB | BB | Total |
| Normal healthy humans | 43 | 37 | 14 | 94 |
| (%) | 45.7 | 39.4 | 14.9 | |
| Myeloma patients | 21 | 21 | 4 | 46 |
| (%) | 45.7 | 45.7 | 8.7 | |
| Myeloma cell lines | 9 | 2 | 0 | |
| (%) | 81.8 | 18.2 | 0 | |

Industrial Applicability

According to the present invention, there was obtained the genomic gene of HM1.24 antigen that is highly expressed in all myeloma cells. The genomic gene that encodes HM1.24 antigen is useful for analysis of HM1.24 antigen. Since HM1.24 antigen is strongly expressed, the promoter region is thought to have a strong promoter activity, and accordingly is useful for the expression of useful genes.

Reference to the microorganisms deposited under the Patent Cooperation Treaty, Rule 13–2, and the name of the Depository organ Depository Organ Name: the National Institute of Bioscience and Human Technology, Agency of Industrial Science and Technology Address: 1–3, Higashi 1-chome, Tsukuba city, Ibaraki pref., Japan Organism (1)

Name: *Escherichia coli* DH5α (pRS38-pUC19)

Accession number: FERM BP-4434

Date deposited: Oct. 5, 1993

Organism (2)

Name: Mouse-mouse hybridoma HM1.24

Accession number: FERM BP-5233

Date deposited: Sep. 14, 1995

What is claimed is:

1. A recombinant promoter sequence DNA having the nucleotide sequence of the 5'-non-coding region as set forth in SEQ ID NO: 4.

2. A recombinant DNA wherein a nucleic acid is operably linked to the DNA having a promoter activity according to claim 1.

3. The recombinant DNA according to claim 2 wherein said nucleic acid encodes a useful protein.

4. A vector comprising the recombinant DNA according to claim 2.

5. The vector according to claim 4 wherein the vector is a plasmid vector or a virus vector.

6. An isolated animal cell into which the recombinant DNA according to claim 2 has been introduced.

7. An isolated animal cell transformed with the vector according to claim 4.

8. A method of expressing a gene which method comprises culturing an isolated animal cell into which the recombinant DNA according to claim 3 has been introduced.

9. A method of producing a protein which method comprises culturing an isolated animal cell transformed with an expression vector comprising a nucleic acid encoding a useful protein operably linked to the DNA according to claim 1.

10. A vector comprising the recombinant DNA according to claim 3.

11. The vector according to claim 10 wherein the vector is a plasmid vector or a virus vector.

* * * * *

SEQUENCE LISTING

<160> NUMBER OF SEQ ID NOS: 33

<210> SEQ ID NO 1
<211> LENGTH: 1014
<212> TYPE: DNA
<213> ORGANISM: Mus sp.
<220> FEATURE:
<221> NAME/KEY: CDS
<222> LOCATION: (23)..(562)

<400> SEQUENCE: 1

```
gaattcggca cgagggatct gg atg gca tct act tcg tat gac tat tgc aga        52
                        Met Ala Ser Thr Ser Tyr Asp Tyr Cys Arg
                         1               5                  10 gtg ccc atg gaa gac ggg gat aag cgc tgt aag ctt ctg ctg ggg ata        100
Val Pro Met Glu Asp Gly Asp Lys Arg Cys Lys Leu Leu Leu Gly Ile
             15                  20                  25 gga att ctg gtg ctc ctg atc atc gtg att ctg ggg gtg ccc ttg att       148
Gly Ile Leu Val Leu Leu Ile Ile Val Ile Leu Gly Val Pro Leu Ile
         30                  35                  40 atc ttc acc atc aag gcc aac agc gag gcc tgc cgg gac ggc ctt cgg       196
Ile Phe Thr Ile Lys Ala Asn Ser Glu Ala Cys Arg Asp Gly Leu Arg
     45                  50                  55 gca gtg atg gag tgt cgc aat gtc acc cat ctc ctg caa caa gag ctg       244
Ala Val Met Glu Cys Arg Asn Val Thr His Leu Leu Gln Gln Glu Leu
 60                  65                  70 acc gag gcc cag aag ggc ttt cag gat gtg gag gcc cag gcc gcc acc       292
Thr Glu Ala Gln Lys Gly Phe Gln Asp Val Glu Ala Gln Ala Ala Thr
 75                  80                  85                  90 tgc aac cac act gtg atg gcc cta atg gct tcc ctg gat gca gag aag       340
Cys Asn His Thr Val Met Ala Leu Met Ala Ser Leu Asp Ala Glu Lys
                 95                 100                 105 gcc caa gga caa aag aaa gtg gag gag ctt gag gga gag atc act aca       388
Ala Gln Gly Gln Lys Lys Val Glu Glu Leu Glu Gly Glu Ile Thr Thr
             110                 115                 120 tta aac cat aag ctt cag gac gcg tct gca gag gtg gag cga ctg aga       436
Leu Asn His Lys Leu Gln Asp Ala Ser Ala Glu Val Glu Arg Leu Arg
         125                 130                 135 aga gaa aac cag gtc tta agc gtg aga atc gcg gac aag aag tac tac       484
Arg Glu Asn Gln Val Leu Ser Val Arg Ile Ala Asp Lys Lys Tyr Tyr
     140                 145                 150 ccc agc tcc cag gac tcc agc tcc gct gcg gcg ccc cag ctg ctg att       532
Pro Ser Ser Gln Asp Ser Ser Ser Ala Ala Ala Pro Gln Leu Leu Ile
155                 160                 165                 170 gtg ctg ctg ggc ctc agc gct ctg ctg cag tgagatccca ggaagctggc         582
Val Leu Leu Gly Leu Ser Ala Leu Leu Gln
                175                 180 acatcttgga aggtccgtcc tgctcggctt ttcgcttgaa cattcccttg atctcatcag      642
ttctgagcgg gtcatggggc aacacggtta gcggggagag cacggggtag ccggagaagg      702
gcctctggag caggtctgga ggggccatgg ggcagtcctg ggtgtgggga cacagtcggg      762
ttgacccagg gctgtctccc tccagagcct ccctccggac aatgagtccc ccctcttgtc      822
tcccaccctg agattgggca tggggtgcgg tgtgggggc atgtgctgcc tgttgttatg       882
ggtttttttt gcgggggggg ttgctttttt ctgggtcttt tgagctccaa aaaaataaac      942
acttcctttg agggagagca caccttaaaa aaaaaaaaa aaaaaaaaa aaaaaattc         1002 gggcggccgc ca                                                          1014
```

<210> SEQ ID NO 2
<211> LENGTH: 2337
<212> TYPE: DNA
<213> ORGANISM: Mus sp.

<400> SEQUENCE: 2

| | | | | | |
|---|---|---|---|---|---|
| ccctccccta | actccaggcc | agactccttt | cagctaaagg | ggagatctgg | atggcatcta | 60 |
| cttcgtatga | ctattgcaga | gtgcccatgg | aagacgggga | taagcgctgt | aagcttctgc | 120 |
| tggggatagg | aattctggtg | ctcctgatca | tcgtgattct | ggggtgccc | ttgattatct | 180 |
| tcaccatcaa | ggccaacagc | gaggcctgcc | gggacggcc | tcgggcagtg | atggagtgtc | 240 |
| gcaatgtcac | ccatctcctg | caacaagagc | tgaccgaggc | ccagaagggc | tttcaggatg | 300 |
| tggaggccca | ggccgccacc | tgcaaccaca | ctgtggtaag | ctcctcaact | cctttggatg | 360 |
| gcctagtact | aggcggtggg | agggacaaga | atctctcccc | agaaatctga | cccagggtgg | 420 |
| gtctccaggg | agatgcaggg | gaggtcctga | aactgctcct | gggcccccac | atcaagggac | 480 |
| ctaggttccc | ctaccagggt | ttgtgggccc | ctaacccagt | ccagggcact | ggtgtagggg | 540 |
| cagggtgtta | aaactctcca | gatccccaa | atcggggacc | tcagtatccc | cctgggactt | 600 |
| aggtgaattt | ataaattctt | tccagggcac | tggtgtcggg | ggccttgaaa | ctcctcgtgg | 660 |
| gcaccagtcc | tggggagta | gaaatcccta | ttcaggttg | aagggggacc | tcaccagacc | 720 |
| ctgaaaaagg | gggcttttga | aattttcact | tcatccctaa | gaaactgaaa | tattcacctg | 780 |
| ggtcctgata | tgggggatct | tgaaactctc | gctgggcatg | tcacttgggc | ggggaaatcc | 840 |
| cactgcattc | tggatttggt | agggccctct | aacttttctt | gggccattgc | tcaggcaatc | 900 |
| tggaaatgtc | cactaaactt | tggttatcga | tagcctccaa | gtttccacgt | ggggtggcct | 960 |
| caaaactccc | attttgagga | cccacatgct | tatgggtggc | cctgggagag | tgtgtggttg | 1020 |
| tggctgttct | ttaaggttgg | agaccatggt | gcagagaggg | ttggaagaaa | acctgaaagg | 1080 |
| ggtttgcatt | taagcccctc | tgtccccagg | acctaggag | gaggcccagg | tcccaggggc | 1140 |
| agcagccaaa | ctccccaggc | caaaaccca | gattctaact | cttcttagat | ggccctaatg | 1200 |
| gcttccctgg | atgcagagaa | ggcccaagga | caaaagaaag | tggaggagct | tgagggtgag | 1260 |
| aaagggagaa | gggagagggc | cggggagggg | tgagtcaggt | atggaagagg | gggtgggggc | 1320 |
| agggagacca | gggctggagg | ttgggtaag | ggggaggttc | tgtcccagag | tggagcaggg | 1380 |
| ccccagcatg | gccacatgct | gacccgcccc | ctgtttctgt | cctcccaccc | taccaggaga | 1440 |
| gatcactaca | ttaaaccata | agcttcagga | cgcgtctgca | gaggtggagc | gactgaggtc | 1500 |
| agagatagcc | ttccccgct | accctccacc | tgccacattc | ctctcacccc | cacatcccta | 1560 |
| gcccaagacc | caggatctcc | tttgctccca | aaatccccat | tgcccaagg | gataaagttt | 1620 |
| gagtcccaca | aaaggataac | ttagcccta | gggtcacaga | gccatgggtg | gccgctgtcc | 1680 |
| attccctccc | cggtgacttg | gattgggcg | gtgcgggggg | aactcccggg | ggcggtgggc | 1740 |
| ttacagggag | ggcggcagga | gccaggacga | gcagatgcct | gatttgcccc | catctgtacc | 1800 |
| gcagaagaga | aaaccaggtc | ttaagcgtga | gaatcgcgca | caagaagtac | tacccccagct | 1860 |
| cccaggactc | cagctccgct | gcggcgcccc | agctgctgat | tgtgctgctg | ggcctcagcg | 1920 |
| ctctgctgca | gtgagatccc | aggaagctgg | cacatcttgg | aaggtccgtc | ctgctcggct | 1980 |
| tttcgcttga | acattcccttt | gatctcatca | gttctgagcg | ggtcatgggg | caacacggtt | 2040 |
| agcggggaga | gcacggggta | gccggagaag | ggcctctgga | gcaggtctgg | agggccatg | 2100 |
| ggcagtcct | gggtgtgggg | acacagtcgg | gttgacccag | ggctgtctcc | ctccagagcc | 2160 |

-continued

| | | | | |
|---|---|---|---|---|
| tccctccgga | caatgagtcc | ccctcttgt | ctcccaccct | gagattgggc | atggggtgcg | 2220 |
| gtgtggggg | catgtgctgc | ctgttgttat | gggtttttt | tgcggggggg | gttgctttt | 2280 |
| tctggggtct | ttgagctcca | aaaaaataaa | cacttcctt | gagggagagc | acacctt | 2337 |

<210> SEQ ID NO 3
<211> LENGTH: 180
<212> TYPE: PRT
<213> ORGANISM: Mus sp.

<400> SEQUENCE: 3

Met Ala Ser Thr Ser Tyr Asp Tyr Cys Arg Val Pro Met Glu Asp Gly
 1               5                  10                  15
Asp Lys Arg Cys Lys Leu Leu Leu Gly Ile Gly Ile Leu Val Leu Leu
                20                  25                  30
Ile Ile Val Ile Leu Gly Val Pro Leu Ile Ile Phe Thr Ile Lys Ala
            35                  40                  45
Asn Ser Glu Ala Cys Arg Asp Gly Leu Arg Ala Val Met Glu Cys Arg
        50                  55                  60
Asn Val Thr His Leu Leu Gln Gln Glu Leu Thr Glu Ala Gln Lys Gly
    65                  70                  75                  80
Phe Gln Asp Val Glu Ala Gln Ala Ala Thr Cys Asn His Thr Val Met
                85                  90                  95
Ala Leu Met Ala Ser Leu Asp Ala Glu Lys Ala Gln Gly Gln Lys Lys
                100                 105                 110
Val Glu Glu Leu Glu Gly Glu Ile Thr Thr Leu Asn His Lys Leu Gln
            115                 120                 125
Asp Ala Ser Ala Glu Val Glu Arg Leu Arg Arg Glu Asn Gln Val Leu
        130                 135                 140
Ser Val Arg Ile Ala Asp Lys Lys Tyr Tyr Pro Ser Ser Gln Asp Ser
145                 150                 155                 160
Ser Ser Ala Ala Ala Pro Gln Leu Leu Ile Val Leu Leu Gly Leu Ser
                165                 170                 175
Ala Leu Leu Gln
            180

<210> SEQ ID NO 4
<211> LENGTH: 2061
<212> TYPE: DNA
<213> ORGANISM: Mus sp.

<400> SEQUENCE: 4

| | | | | |
|---|---|---|---|---|
| actaaaagtc | tctgatatgc | agaaataatg | gcataagctg | tctttctgtc | tgtcccctct | 60 |
| ctctctctct | gcctcggctg | ccaggcaggg | aagggccccc | tgtccagtgg | acacgtgacc | 120 |
| cacatgacct | tacctatcat | tggagatgac | tcacactctt | taccctgccc | cttttgcttt | 180 |
| gtatccaata | aataacagca | cagccagaca | ttcggggcca | ctaccagtct | ccgcgcattg | 240 |
| ctggtagtgg | tcccccgggc | cagctgtct | tttcttttat | ctcttcgtct | tgtgtcttta | 300 |
| tttctacact | ctctcgtcgc | cgcacacagg | gagagaccca | ctgaccctgt | ggggctggtc | 360 |
| cctacagtaa | ttttaaaggg | aagagcaaca | aactttcggt | ttgcagggct | gggactgttt | 420 |
| acagctgcaa | aatttagaga | ggacatcaat | ctattattat | ccacattta | cagctgggga | 480 |
| aatcaatgct | aagagaggaa | attcatttgc | cagaggtgc | accacctgg | cctccaatgt | 540 |
| gcaattcatg | caattgtgat | ttccgacctg | gtcccaaact | aaccctaaag | ttagcaggcc | 600 |

```
agaacagtgc tgctcaaata agtcagctta gtcaaataag tcaggcaaag gtcgtgtctt      660
tgcacctgga gtcctggcca ggctggtagg tccctcctcc tgggacaagt tcaccctcag      720
aattttcagc aagatcatct cccacagctt gttaattggt tcttggttct aagtgatttt      780
tttgtttatt ggtttaagag atgggatccc actctatcac ccaggcttga gtgccgtggc      840
acaatcatag ctcgctgcag cctcaaactc ctgggctcga gtgatcctcc tgcctcagcc      900
tcccagcctc agcctgggac cacaggcatg taccaccatg cctggctcta agtggcttta      960
atggggtcct tctgagggat gttggagtca gggcctgggg ggagttcccc aggccttctg     1020
ggaggcctgg gctctggact tgacctcgcc tactgtctgg ccctgctgaa agaaaaaaa      1080 aacatggaaa tggcagacct aacagaatct gggctgtggt caggatgtgg ctgaagaagc     1140
cacaagaaaa acatgcagtc ccctttcagc ggtcatgccc agcagttggg tgccgataat     1200
gggcctgatt tcctgtagga agccctggct ctcttggcca catggacagt gtctgaggct     1260
ggccctgtta ttccccttg cagatgaaga aacaggctca gagagtttac ctggtatcct     1320
ggagtcccag gagcactttt tctggaagta ggagcttgtt tcctgcaggt gccaagacag     1380
agaccgacat tgtttgttgg ctgggtcggt ctcccagttt tcagctggct ccagtctcac     1440
ctgttgctca cacaccctcc atgtctccca tagtcccctc ggtggggaca gaggcactgg     1500
atgaagccct gctcgtcacc acagagacac ctgaacacaa aaaccagtcc ctggggtcag     1560
acccaggccc cgcccccaga cccaggccct gccctcactc caccacgcaa ctgtgcaacc     1620
tcagtttccc caggtggaga ccggaccaac aatgatggcc tctgcctctt caggtcatag     1680
tacagatgaa tacaggctgg cacggcctag gcactcagta acacacggca gaggcacagg     1740
gacttaagat ggagtgtccc aggcagccac agttggctgg cacccagttg ggaagggccc     1800
aagggctttt aaagcagggt gaaaaaaaa gcccacctcc tttctgggaa actgaaactg     1860
aaaacctaat taatcctctg cctgtaggtg cctcatgcaa gagctgctgg tcagagcact     1920
tcctggaact tgctattggt caggacgttt cctatgctaa taaaggggtg gcccgtagaa     1980
gattccagca ccctccccta actccaggcc agactccttt cagctaaagg ggagatctgg     2040
atggcatcta cttcgtatga c                                                2061

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 5
gtaatacgac tcactatagg gc                                                 22

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 6
atccccgtct tccatgggca ctctgca                                            27

<210> SEQ ID NO 7
<211> LENGTH: 19
<212> TYPE: DNA
<213> ORGANISM: Artificial Sequence
```

```
<220> FEATURE:
<223> OTHER INFORMATION: Description of Artificial Sequence: Primer

<400> SEQUENCE: 7
actatagggc acgcgtggt                                                    19

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 8
atagtcatac gaagtagatg ccatccag                                          28

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 9
actatagggc acgcgtggt                                                    19

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 10
cctcgctgtt ggccttgatg gtgaa                                             25

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 11
gccaacagcg aggcctgc                                                     18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 12
gcatccaggg aagccatt                                                     18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 13
actccccagg ccaaaacc                                                     18
```

```
<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 14
cgcgtcctga agcttatggt tt                                              22

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 15
gcgtctgcag cggtggag                                                   18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 16
cgaaaagccg agcaggac                                                   18

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 17
atggcatcta cttcgtatga c                                               21

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 18
aaccgtgttg ccccatga                                                   18

<210> SEQ ID NO 19
<211> LENGTH: 471
<212> TYPE: DNA
<213> ORGANISM: Mus sp.
<220> FEATURE:
<221> NAME/KEY: CDS
<222> LOCATION: (1)..(468)

<400> SEQUENCE: 19 atg gca tct act tcg tat gac tat tgc aga gtg ccc atg gaa gac ggg      48
Met Ala Ser Thr Ser Tyr Asp Tyr Cys Arg Val Pro Met Glu Asp Gly
 1               5                  10                  15 gat aag cgc tgt aag ctt ctg ctg ggg ata gga att ctg gtc ctc ctg      96
Asp Lys Arg Cys Lys Leu Leu Leu Gly Ile Gly Ile Leu Val Leu Leu
             20                  25                  30
```

```
atc atc gtg att ctg ggg gtg ccc ttg att atc ttc acc atc aag gcc    144
Ile Ile Val Ile Leu Gly Val Pro Leu Ile Ile Phe Thr Ile Lys Ala
         35                  40                  45 aac agc gag gcc tgc cgg gac ggc ctt cgg gca gtg atg gag tgt cgc    192
Asn Ser Glu Ala Cys Arg Asp Gly Leu Arg Ala Val Met Glu Cys Arg
 50                  55                  60 aat gtc acc cat ctc ctg caa caa gag ctg acc gag gcc cag aag ggc    240
Asn Val Thr His Leu Leu Gln Gln Glu Leu Thr Glu Ala Gln Lys Gly
 65                  70                  75                  80 ttt cag gat gtg gag gcc cag gcc gcc acg tgc aac cac act gtg aag    288
Phe Gln Asp Val Glu Ala Gln Ala Ala Thr Cys Asn His Thr Val Lys
                 85                  90                  95 aga aaa cca ggt ctt aag cgt gag aat cgc gga caa gaa gta cta ccc    336
Arg Lys Pro Gly Leu Lys Arg Glu Asn Arg Gly Gln Glu Val Leu Pro
            100                 105                 110 cag ctc cca gga ctc cag ctc cgc tgc ggc gcc cca gct gct gat tgt    384
Gln Leu Pro Gly Leu Gln Leu Arg Cys Gly Ala Pro Ala Ala Asp Cys
        115                 120                 125 gct gct ggg cct cag cgc tct gct gca gtg aga tcc cag gaa gct ggc    432
Ala Ala Gly Pro Gln Arg Ser Ala Ala Val Arg Ser Gln Glu Ala Gly
    130                 135                 140 aca tct tgg aag gtc cgt cct gct cgg ctt ttc gct tga                471
Thr Ser Trp Lys Val Arg Pro Ala Arg Leu Phe Ala
145                 150                 155
```

<210> SEQ ID NO 20
<211> LENGTH: 156
<212> TYPE: PRT
<213> ORGANISM: Mus sp.

<400> SEQUENCE: 20

```
Met Ala Ser Thr Ser Tyr Asp Tyr Cys Arg Val Pro Met Glu Asp Gly
 1               5                  10                  15

Asp Lys Arg Cys Lys Leu Leu Leu Gly Ile Gly Ile Leu Val Leu Leu
            20                  25                  30

Ile Ile Val Ile Leu Gly Val Pro Leu Ile Ile Phe Thr Ile Lys Ala
         35                  40                  45

Asn Ser Glu Ala Cys Arg Asp Gly Leu Arg Ala Val Met Glu Cys Arg
 50                  55                  60

Asn Val Thr His Leu Leu Gln Gln Glu Leu Thr Glu Ala Gln Lys Gly
 65                  70                  75                  80

Phe Gln Asp Val Glu Ala Gln Ala Ala Thr Cys Asn His Thr Val Lys
                 85                  90                  95

Arg Lys Pro Gly Leu Lys Arg Glu Asn Arg Gly Gln Glu Val Leu Pro
            100                 105                 110

Gln Leu Pro Gly Leu Gln Leu Arg Cys Gly Ala Pro Ala Ala Asp Cys
        115                 120                 125

Ala Ala Gly Pro Gln Arg Ser Ala Ala Val Arg Ser Gln Glu Ala Gly
    130                 135                 140

Thr Ser Trp Lys Val Arg Pro Ala Arg Leu Phe Ala
145                 150                 155
```

<210> SEQ ID NO 21
<211> LENGTH: 7
<212> TYPE: PRT
<213> ORGANISM: Mus sp.

<400> SEQUENCE: 21

Met Ala Ser Thr Ser Tyr Asp

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 22
tccatgtccc ctcggtgg                                           18

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 23
atagtcatac gaagtagatg ccatccag                                28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 24
aaaggtacca gctgtctttc tgtctgtc                                28

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 25
gtgctctccc cgctaacc                                           18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 26
ggacgtttcc tatgctaa                                           18

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 27
aaagcggccg ctcatcactg cagcagagcg ctgag                        35

<210> SEQ ID NO 28
<211> LENGTH: 18
<212> TYPE: DNA
<213> ORGANISM: Artificial Sequence

```
<220> FEATURE:
<223> OTHER INFORMATION: Description of Artificial Sequence: Primer

<400> SEQUENCE: 28
aggggaactc accagacc                                                    18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 29
atggccctaa tggcttcc                                                    18

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 30
cattaaacca taagcttcag g                                                21

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 31
ccctcaagct cctccact                                                    18

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 32
gacggatcct aaagcttaca gcgcttatc                                        29

<210> SEQ ID NO 33
<211> LENGTH: 2456
<212> TYPE: DNA
<213> ORGANISM: Mus sp.

<400> SEQUENCE: 33
tcccatagtc ccctcggtgg ggacagaggc actggatgaa gccctgctcg tcaccacaga      60
gacacctgaa cacaaaaacc agtccctggg gtcagaccca ggccccgccc ccagacccag     120
gccctgccct cactccacca cgcaactgtg caacctcagt ttccccaggt ggagaccgga     180
ccaacaatga tggcctctgc ctcttcaggt catagtacag atgaatacag gctggcacgg     240
cctaggcact cagtaacaca cggcagaggc acagggactt aagatggagt gtcccaggca     300
gccacagttg gctggcaccc agttgggaag ggcccaaggg cttttaaagc agggtgaaaa     360
aaaaagccca cctcctttct gggaaactga aactgaaaac ctaattaatc ctctgcctgt     420
aggtgcctca tgcaagagct gctggtcaga gcacttcctg gaacttgcta ttggtcagga     480
```

-continued

```
cgtttcctat gctaataaag gggtggcccg tagaagattc cagcaccctc ccctaactcc    540
aggccagact cctttcagct aaaggggaga tctggatggc atctacttcg tatgactatt    600
gcagagtgcc catggaagac ggggataagc gctgtaagct tctgctgggg ataggaattc    660
tggtgctcct gatcatcgtg attctggggg tgcccttgat tatcttcacc atcaaggcca    720
acagcgaggc ctgccgggac ggccttcggg cagtgatgga gtgtcgcaat gtcacccatc    780
tcctgcaaca agagctgacc gaggcccaga agggctttca ggatgtggag gcccaggccg    840
ccacctgcaa ccacactgtg gtaagctcct caactccttt ggatggccta gtactaggcg    900
gtgggaggga caagaatctc tccccagaaa tctgacccag ggtgggtctc caggagatg     960
caggggaggt cctgaaactg ctcctgggcc cccacatcaa gggacctagg ttcccctacc   1020
agggtttgtg ggcccctaac ccagtccagg gcactggtgt aggggcaggg tgttaaaact   1080
ctccagatcc cccaaatcgg ggacctcagt atcccctgg  gacttaggtg aatttataaa   1140
ttctttccag ggcactggtg tcgggggcct tgaaactcct cgtgggcacc agtcctgggg   1200
gagtagaaat ccctattcag ggttgaaggg ggacctcacc agaccctgaa aaaggggct    1260
tttgaaattt tcacttcatc cctaagaaac tgaaatattc acctgggtcc tgatatgggg   1320
gatcttgaaa ctctcgctgg gcatgtcact tgggcgggga aatcccactg cattctggat   1380
ttggtagggc cctctaactt ttcttgggcc attgctcagg caatctggaa atgtccacta   1440
aactttggtt atcgatagcc tccaagtttc cacgtgggt  ggcctcaaaa ctcccatttt   1500
gaggacccac atgcttatgg gtggccctgg gagagtgtgt ggttgtggct gttctttaag   1560
gttggagacc atggtgcaga gagggttgga agaaaacctg aaagggggttt gcatttaagc   1620
ccctctgtcc ccaggaccta gggaggaggc ccaggtccca ggggcagcag ccaaactccc   1680
caggccaaaa ccccagattc taactcttct tagatggccc taatggcttc cctggatgca   1740
gagaaggccc aaggacaaaa gaaagtggag gagcttgagg gtgagaaagg gagaagggag   1800
agggccgggg agggggtgagt caggtatgga agaggggtg ggggcaggga gaccagggct   1860
ggaggttggg gtaaggggga ggttctgtcc cagagtggag cagggcccca gcatggccac   1920
atgctgaccc gcccctgtt  tctgtcctcc caccctacca ggagagatca ctacattaaa   1980
ccataagctt caggacgcgt ctgcagaggt ggagcgactg aggtcagaga tagccttccc   2040
ccgctaccct ccacctgcca cattcctctc accccacat  ccctagccca agacccagga   2100
tctcctttgc tcccaaaatc cccattgccc caagggataa agtttgagtc ccacaaaagg   2160
ataacttagc ccctagggtc acagagccat gggtggccgc tgtccattcc ctccccggtg   2220
acttggattg gggcggtgcg gggggaactc ccggggcgg  tgggcttaca gggagggcgg   2280
caggagccag gacgagcaga tgcctgattt gccccatct  gtaccgcaga agagaaaacc   2340
aggtcttaag cgtgagaatc gcggacaaga agtactaccc cagctcccag gactccagct   2400
ccgctgcggc gccccagctg ctgattgtgc tgctgggcct cagcgctctg ctgcag       2456
```